(12) United States Patent
Schraeml et al.

(10) Patent No.: US 10,414,818 B2
(45) Date of Patent: Sep. 17, 2019

(54) ***THERMUS THERMOPHILUS* SLYD FKBP DOMAIN SPECIFIC ANTIBODIES**

(71) Applicant: Roche Diagnostics Operations, Inc., Indianapolis, IN (US)

(72) Inventors: Michael Schraeml, Penzberg (DE); David Casagolda Vallribera, Barcelona (ES); Frank Kroner, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 297 days.

(21) Appl. No.: 15/025,230

(22) PCT Filed: Sep. 22, 2014

(86) PCT No.: PCT/EP2014/070123
§ 371 (c)(1),
(2) Date: Mar. 25, 2016

(87) PCT Pub. No.: WO2015/044083
PCT Pub. Date: Apr. 2, 2015

(65) Prior Publication Data
US 2016/0237144 A1   Aug. 18, 2016

(30) Foreign Application Priority Data

Sep. 27, 2013   (EP) ..................................... 13186398

(51) Int. Cl.
*C07K 16/12* (2006.01)
*G01N 33/577* (2006.01)

(52) U.S. Cl.
CPC ....... *C07K 16/1203* (2013.01); *G01N 33/577* (2013.01); *C07K 2317/34* (2013.01); *C07K 2317/56* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,737,456 A | 4/1988 | Weng et al. | |
| 4,816,567 A | 3/1989 | Cabilly et al. | |
| 5,571,894 A | 11/1996 | Wels et al. | |
| 5,587,458 A | 12/1996 | King et al. | |
| 5,648,237 A | 7/1997 | Carter | |
| 5,750,373 A | 5/1998 | Garrard et al. | |
| 5,789,199 A | 8/1998 | Joly et al. | |
| 5,840,523 A | 11/1998 | Simmons et al. | |
| 5,869,046 A | 2/1999 | Presta et al. | |
| 5,959,177 A | 9/1999 | Hein et al. | |
| 6,040,498 A | 3/2000 | Stomp et al. | |
| 6,194,551 B1 | 2/2001 | Idusogie et al. | |
| 6,417,429 B1 | 7/2002 | Hein et al. | |
| 6,420,548 B1 | 7/2002 | Vezina et al. | |
| 7,125,978 B1 | 10/2006 | Vezina et al. | |
| 7,521,541 B2 | 4/2009 | Eigenbrot et al. | |
| 2005/0079574 A1 | 4/2005 | Bond | |
| 2005/0119455 A1 | 6/2005 | Fuh et al. | |
| 2005/0266000 A1 | 12/2005 | Bond et al. | |
| 2007/0117126 A1 | 5/2007 | Sidhu et al. | |
| 2007/0160598 A1 | 7/2007 | Dennis et al. | |
| 2007/0237764 A1 | 10/2007 | Birtalan et al. | |
| 2007/0292936 A1 | 12/2007 | Barthelemy et al. | |
| 2009/0002360 A1 | 1/2009 | Chen et al. | |

FOREIGN PATENT DOCUMENTS

| | | |
|---|---|---|
| EP | 040497 A2 | 12/1990 |
| EP | 1516928 A1 | 3/2005 |
| EP | 1621555 A1 | 2/2006 |
| EP | 1025218 B1 | 1/2009 |
| WO | 1993/001161 A1 | 1/1993 |
| WO | 1993/016185 A2 | 8/1993 |
| WO | 1999/051642 A1 | 10/1999 |
| WO | 2003000878 A2 | 1/2003 |
| WO | 2007077008 A1 | 7/2007 |
| WO | 2012150320 A1 | 11/2012 |
| WO | PCT/EP2012/070123 | 12/2014 |

OTHER PUBLICATIONS

Paul. Fundamental Immunology, 3rd Edition, Raven Press, New York, Chapter 8, pp. 292-295, 1993 (Year: 1993).*
MacCallum et al. Antibody-antigen Interactions: Contact Analysis and Binding Site Topography. Journal of Molecular Biology, 262: 732-745, 1996 (Year: 1996).*
Casset et al. A peptide mimetic of an anti-CD4 monoclonal antibody by rational design. Biochemical and Biophysical Research Communications, 307:198-205, 2003 (Year: 2003).*
Vajdos et al. Comprehensive Functional Maps of the Antigen-binding Site of an Anti-ErbB2 Antibody Obtained with Shotgun Scanning Mutagenesis. Journal of Molecular Biology, Jul. 5, 2002;320(2):415-28 (Year: 2002).*
Brown et al. Tolerance to Single, but Not Multiple, Amino Acid Replacements in Antibody VH CDR2. Journal of Immunology. May 1996; 156(9):3285-91 (Year: 1996).*
Rudikoff et al. Single amino acid substitution altering antigen-binding specificity. Proc. Natl. Acad. Sci. USA, 79(6):1979-1983, Mar. 1982 (Year: 1982).*
Colman. Effects of amino acid sequence changes on antibody-antigen interactions. Research in Immunology, 145:33-36, 1994 (Year: 1994).*
Kindt, Thomas J. et al., CDRs Bind Antigen Conformational Changes May be Inducted by Antigen Binding, Kuby Immunology, 2007, 90-91, Sixth Edition, W. H. Freeman and Company, New York.
Binz, H. Kaspar et al., Engineering novel binding proteins from nonimmunoglobulin domains, Nature Biotechnology, 2005, pp. 1257-1268, vol. 23, No. 10.

(Continued)

*Primary Examiner* — Vanessa L. Ford
*Assistant Examiner* — Sandra E Dillahunt
(74) *Attorney, Agent, or Firm* — Roche Diagnostics Operations, Inc.

(57) ABSTRACT

The present description relates to anti-*Thermus thermophilus* SlyD FKBP domain antibodies and methods of using the same.

3 Claims, 9 Drawing Sheets
Specification includes a Sequence Listing.

(56) References Cited

OTHER PUBLICATIONS

Brecht, S. et al. Changes in Peptidyl-Prolyl CIS/Trans Isomerase Activity and FK506 Binding Protein Expression Following Neuroprotection by FK506 in the Ischemic Rat Brain, Neuroscience, 2003, pp. 1037-1048, vol. 120.
Charlton, Keith A., Expression and Isolation of Recombinant Antibody Fragments in E. coli, Methods in Molecular Biology, 2003, pp. 245-254, vol. 248.
Chen et al, 1999, "Selection and Analysis of an Optimized Anti-Vegf Antibody: Crystal Structure of an Affinity-matured Fab in Complex with Antigen", Journal of Molecular Biology, 293:865-881.
Chothia, Cyrus and Lesk, Arthur M., Canonical Structures for the Hypervariable Regions of Immunoglobulins, Journal of Molecular Biology, 1987, pp. 901-917, vol. 196.
Chowdhury, Partha S., Engineering Hot Spots for Affinity Enhancement of Antibodies, Methods in Molecular Biology, 2008, pp. 179-196, vol. 207.
Clackson, Tim et al., Making antibody fragments using phage display libraries, Nature, 1991, pp. 624-628, vol. 352.
Cunningham, Brian C. and Wells, James A., High-Resolution Epitope Mapping of hGH-Receptor Interactions by Alanine-Scanning Mutagenesis, Science, 1989, pp. 1081-1085, vol. 244.
DeCenzo, Maureen T. et al., FK506-binding protein mutational analysis: defining the active-site residue contributions to catalysis and the stability of ligand complexes, Protein Engineering, 1996, pp. 173-180, vol. 9, No. 2.
Fellouse, Frederic A. et al., Synthetic antibodies from a four-amino-acid code: A dominant role for tyrosine in antigen recognition, P Natl Acad Sci USA, 2004, pp. 12467-12472, vol. 101.
Flatman, Stephen et al., Process analytics for purification of monoclonal antibodies, Journal of Chromatography B, 2007, pp. 79-87, vol. 848.
Graham, F. L et al., Characteristics of a Human Cell Line Transformed by DNA from Human Adenovirus Type 5, Journal of General Virology, 1977, pp. 59-72, vol. 36.
Griffiths, Andrew D. et al., Human anti-self antibodies with high specificity from phage display libraries, The EMBO Journal, 1993, pp. 725-734, vol. 12.
Harlow, Ed and Lane, David, Structure of the Antibody-Antigen Complex, Antibodies: A Laboratory Manual, 1988, pp. 23-26, Chapter 3, Cold Spring Harbor Laboratory Press, NY.
Holliger, Philipp et al., "Diabodies": Small bivalent and bispecific antibody fragments, Proceedings of the National Academy of Sciences USA, 1993, pp. 6444-6448, vol. 90.
Hoogenboom, Hennie R. and Winter, Greg, By-passing Immunisation Human Antibodies from Synthetic Repertoires of Germline VH Gene Segments Rearranged in Vitro, Journal of Molecular Biology, 1992, pp. 381-388, vol. 227.
Hoogenboom, Hennie R., Overview of Antibody Phage-Display Technology and Its Applications, Methods in Molecular Biology, 2002, pp. 1-37, vol. 178.
Hosse, Ralf J. et al., A new generation of protein display scaffolds for molecular recognition, Protein Science, 2006, pp. 14-27, vol. 15.
Hudson, Peter J. and Souriau, Christelle, Engineered antibodies, Nature Medicine, 2003, pp. 129-134, vol. 9, No. 1.
Ideno, A. et al., Expression of foreign proteins in Escherichia coli by fusing with an archaeal FK506 binding protein, Applied Microbiology and Biotechnology, 2004, pp. 99-105, vol. 64.
Idusogie, Esohe E. et al., Mapping of the C1q Binding Site on Rituxan, a Chimeric Antibody with a Human IgG1 Fc, Journal of Immunology, 2000, pp. 4178-4184, vol. 164.
International Search Report dated Dec. 15, 2014, in Application No. PCT/EP2014/070123, 4 pp.
Kabat et al., Sequences of Proteins of Immunological Interest, U. S. Department of Health and Human Services, 1991, pp. 647-723, vol. 1, Fifth Edition, Public Health Service, National Institutes of Health, Bethesda, Maryland.
Kam, Nadine Wong Shi et al., Carbon nanotubes as multifunctional biological transporters and near-infrared agents for selective cancer cell destruction, Proceedings of the National Academies of Science USA, 2005, pp. 11600-11605, vol. 102.
Knappik, Achim et al., Fully Synthetic Human Combinatorial Antibody Libraries (HuCAL) Based on Modular Consensus Frameworks and CDRs Randomized with Trinucleotides, Journal of Molecular Biology, 2000, pp. 57-86, vol. 296.
Lee, Chingwei V. et al., Bivalent antibody phage display mimics natural immunoglobulin, Journal of Immunological Methods, 2004, pp. 119-132, vol. 284.
Lee, Chingwei V. et al., High-affinity Human Antibodies from Phage-displayed Synthetic Fab Libraries with a Single Framework Scaffold, Journal of Molecular Biology, 2004, pp. 1073-1093, vol. 340.
Lightwood, Daniel J. et al., Antibody generation through B cell panning on antigen followed by in situ culture and direct RT-PCR on cells harvested en masse from antigen-positive wells, Journal of Immunological Methods, 2006, pp. 133-143, vol. 316.
MacCallum, Robert M. et al., Antibody-antigen Interactions: Contact Analysis and Binding Site Topography, Journal of Molecular Biology, 1996, pp. 732-745, vol. 262.
Marks, James D. and Bradbury, Andrew, Selection of Human Antibodies from Phage Display Libraries, Methods in Molecular Biology, 2004, pp. 161-176, vol. 248.
Marks, James D. et al., By-passing Immunization Human Antibodies from V-gene Libraries Displayed on Phage, Journal of Molecular Biology, 1991, pp. 581-597, vol. 222.
Mather, Jennie P. et al., Culture of Testicular Cells in Hormone-Supplemented Serum-Free Medium, Annals of the New York Academy of Sciences, 1982, pp. 44-68, vol. 383.
Mather, Jennie P., Establishment and Characterization of Two Distinct Mouse Testicular Epithelial Cell Lines, Biology of Reproduction, 1980, pp. 243-252, vol. 23.
McCafferty, John et al., Phage antibodies: filamentous phage displaying antibody variable domains, Nature, 1990, pp. 552-554, vol. 348.
McNamara, Linda M. Alexander et al., Peptides Constrained by an Aliphatic Linkage between Two Cα Sites: Design, Synthesis, and Unexpected Conformational Properties of an i,(i+4)-Linked Peptide, Journal of Organic Chemistry, 2001, pp. 4585-4594, vol. 66.
Plückthun, A., Antibodies from Escherichia coli, The Pharmacology of Monoclonal Antibodies, 1994, pp. 269-315, vol. 113, Chapter 11.
Portolano, Stefano, Lack of Promiscuity in Autoantigen-Specific H and L Chain Combinations as Revealed by Human H and L Chain "Roulette", The Journal of Immunology, 1993, pp. 880-887, vol. 150, No. 3.
Presta, Leonard G. et al, Humanization of an Anti-Vascular Endothelial Growth Factor Monoclonal Antibody for the Therapy of Solid Tumors and Other Disorders, Cancer Research, 1997, pp. 4593-4599, vol. 57.
Scholz, Christian et al., Autocatalytic Folding of the Folding Catalyst FKBP12, The Journal of Biological Chemistry, 1996, pp. 12703-12707, vol. 271, No. 22.
Scholz, Christian et al., SlyD Proteins from Different Species Exhibit High Prolyl Isomerase and Chaperone Activities, Biochemistry, 2006, pp. 20-33, vol. 45.
Schories, Barbara et al., Multimer formation by FKBP-12: roles for cysteine 23 and phenylalanine 36, Journal of Peptide Science, 2007, pp. 475-480, vol. 13.
Sidhu, Sachdev S. et al., Phage-displayed Antibody Libraries of Synthetic Heavy Chain Complementarity Determining Regions, Journal of Molecular Biology, 2004, pp. 299-310, vol. 338.
Skerra, A., Corrigendum (Engineered protein scaffolds for molecular recognition, Journal of Molecular Recognition 13: 167-187), Journal of Molecular Recognition, 2000, p. 409, vol. 13.
Standaert, Robert F. et al., Molecular cloning and overexpression of the human FK506-binding protein FKBP, Nature, 1990, pp. 671-674, vol. 346.
Suzuki, Rintaro et al., Three-dimensional Solution Structure of an Archaeal FKBP with a Dual Function of Peptidyl Prolyl cis-trans Isomerase and Chaperone-like Activities, Journal of Molecular Biology, 2003, pp. 1149-1160, vol. 328.
Timerman, Anthony P. et al., Characterization of an Exchange Reaction between Soluble FKBP-12 and the FKBP-Ryanodine

(56) References Cited

OTHER PUBLICATIONS

Receptor Complex Modulation by FKBP Mutants Deficient in Peptidyl-Prolyl Isomerase Activity, The Journal of Biological Chemistry, 1995, pp. 2451-2459, vol. 270, No. 6.

Urlaub, Gail and Chasin, Lawrence A., Isolation of Chinese hamster cell mutants deficient in dihydrofolate reductase activity, Proceedings of the National Academy of Sciences USA, 1980, pp. 4216-4220, vol. 77, No. 7.

Winter, Greg et al., Making Antibodies by Phage Display Technology, Annual Review of Immunology, 1994, pp. 433-455, vol. 12.

Yazaki, Paul J. and Wu, Anna M., Expression of Recombinant Antibodies in Mammalian Cell Lines, Methods in Molecular Biology, 2004, pp. 255-268, vol. 248.

Kahra, D. et al., Conformational Plasticity and Dynamics in the Generic Protein Folding Catalyst SlyD Unraveled by Single-Molecule FRET, Journal of Molecular Biology, 2011, 781-790, 411.

Kaluarachchi, H. et al., Nickel Binding and [NiFe]-Hydrogenase Maturation by the Metallochaperone SlyD with a Single Metal-Binding Site in *Escherichia coli*, Journal of Molecular Biology, 2012, 28-35, 417.

Knappe, T.A. et al., Insertion of a Chaperone Domain Converts FKBP12 into a Powerful Catalyst of Protein Folding, J. Mol. Biol., 2007, 1458-1468, 368.

Kovermann, M. et al., NMR relaxation unravels interdomain crosstalk of the two domain prolyl isomerase and chaperone SlyD, Biochimica et Biophysica Acta, 2011, 873-881, 1814.

Loew, C. et al, Crystal Structure Determination and Functional Characterization of the Metallochaperone SlyD from Thermus thermophilus, J. Mol. Biol., 2010, 375-390, 398.

\* cited by examiner

Fig. 1

| Ab | Ab (RU) | Analyte | MR | ka (1/Ms) | kd (1/s) | KD (M) | Chi2 | T(°C) |
|---|---|---|---|---|---|---|---|---|
| 0712pS4D5 | 92 | TtSlyD-A | 1.7 | 3.35E+05 | 1.00E-05 | 2.99E-11 | 0.11 | 25 |
| | 89 | TtSlyD-B | 1.9 | 2.71E+05 | 1.00E-05 | 3.69E-11 | 0.1 | 25 |
| 0612pS3A8 | 223 | TtSlyD-A | 1.2 | 1.27E+06 | 1.00E-05 | 7.87E-12 | 0.05 | 25 |
| | 212 | TtSlyD-B | 1.4 | 4.28E+05 | 1.00E-05 | 2.34E-11 | 0.28 | 25 |

Fig. 4
A
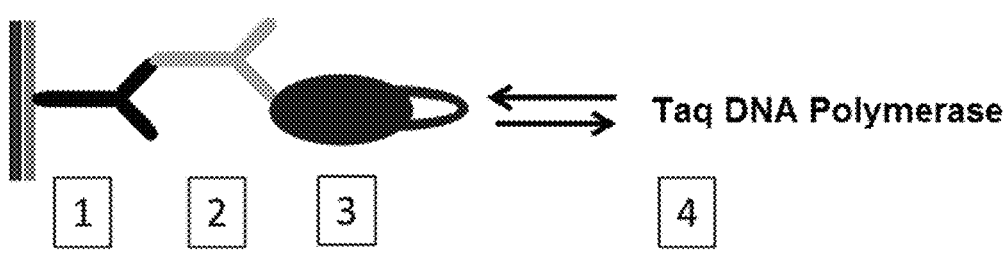
B
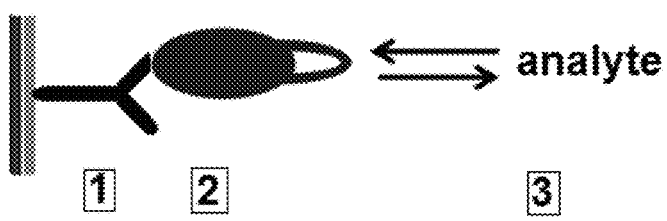

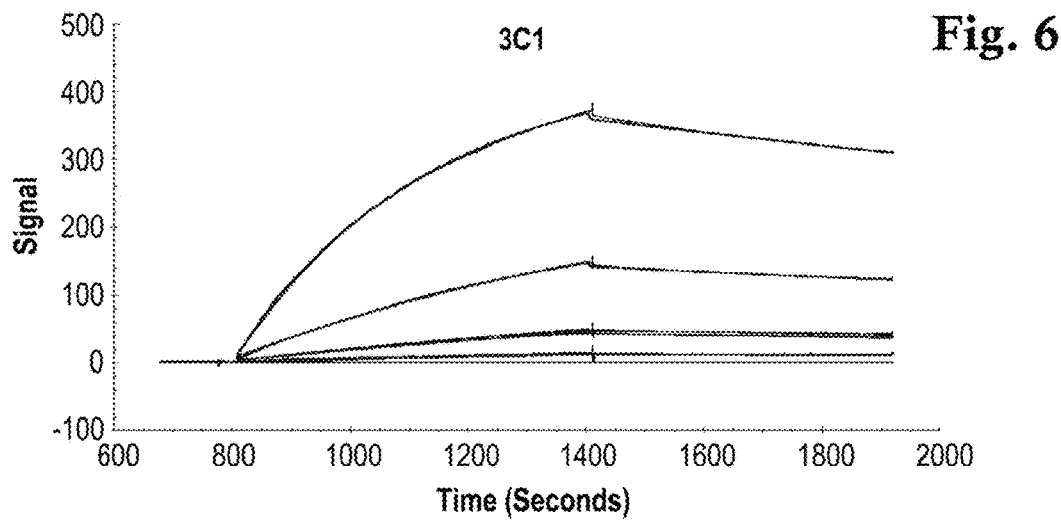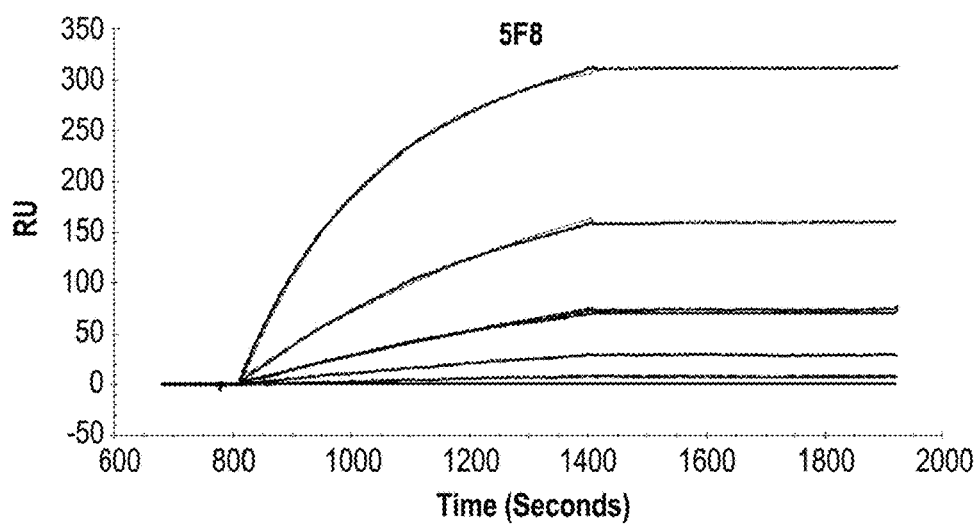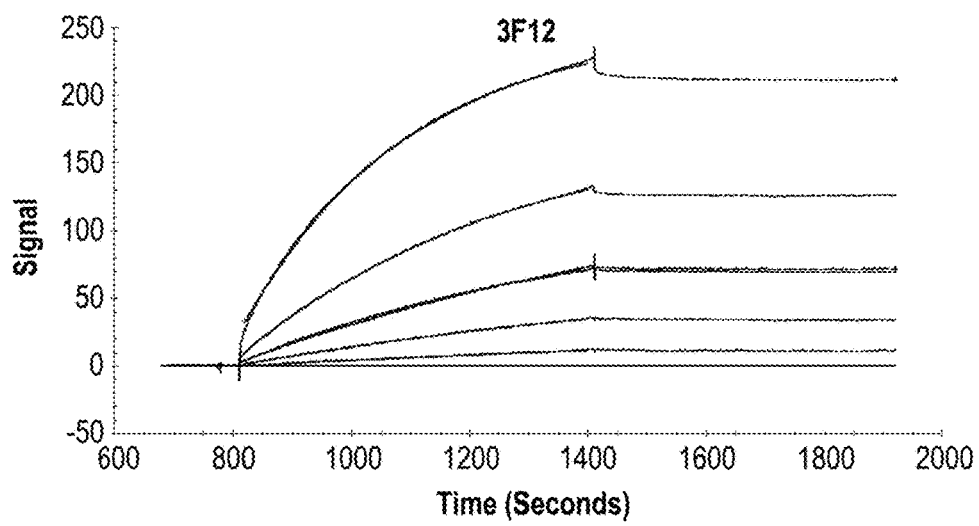
Fig. 6

Fig. 7

| 0712pS4D5 (RU) | scaffold (18 kDa) | scaffold (RU) | MR | analyte | analyte (RU) | MR | ka (1/Ms) | kd (1/s) | KD (M) | Chi2 | T(°C) |
|---|---|---|---|---|---|---|---|---|---|---|---|
| 1268 | 3F12 | 286 | 2 | Taq pol. (93 kDa) | 200 | 0.1 | 1.3E+04 | 1.0E-05 | 7.46E-10 | 1.78 | 25 |
| 1141 | 5F8 | 254 | 2 | | 291 | 0.2 | 1.5E+04 | 1.0E-05 | 6.90E-10 | 1.18 | 25 |
| 1253 | 3C1 | 267 | 2 | | 330 | 0.2 | 9.5E+03 | 2.9E-04 | 3.05E-08 | 1.03 | 25 |

Fig. 8
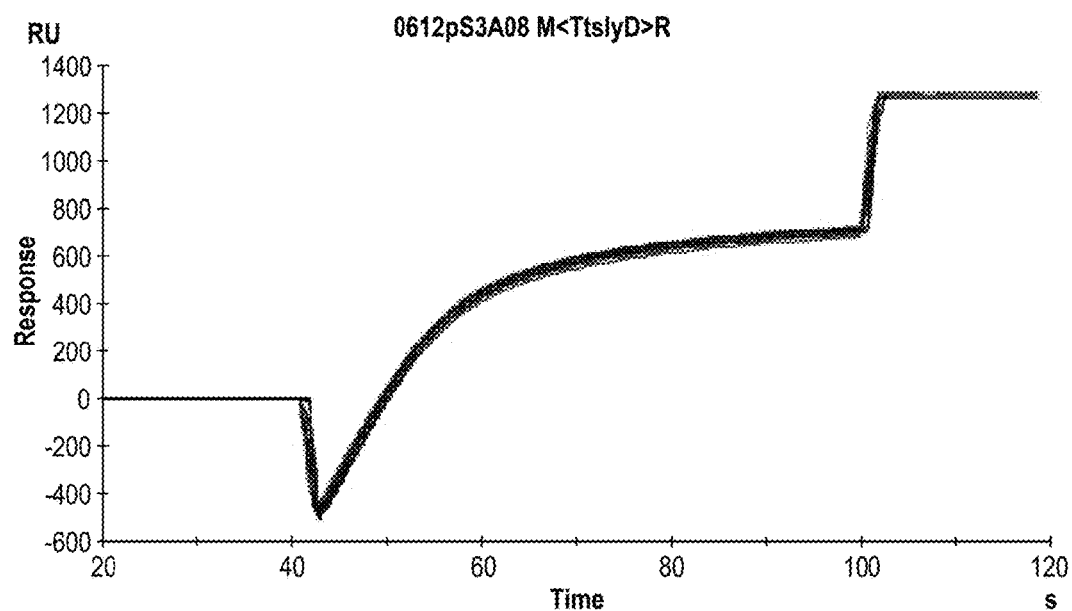
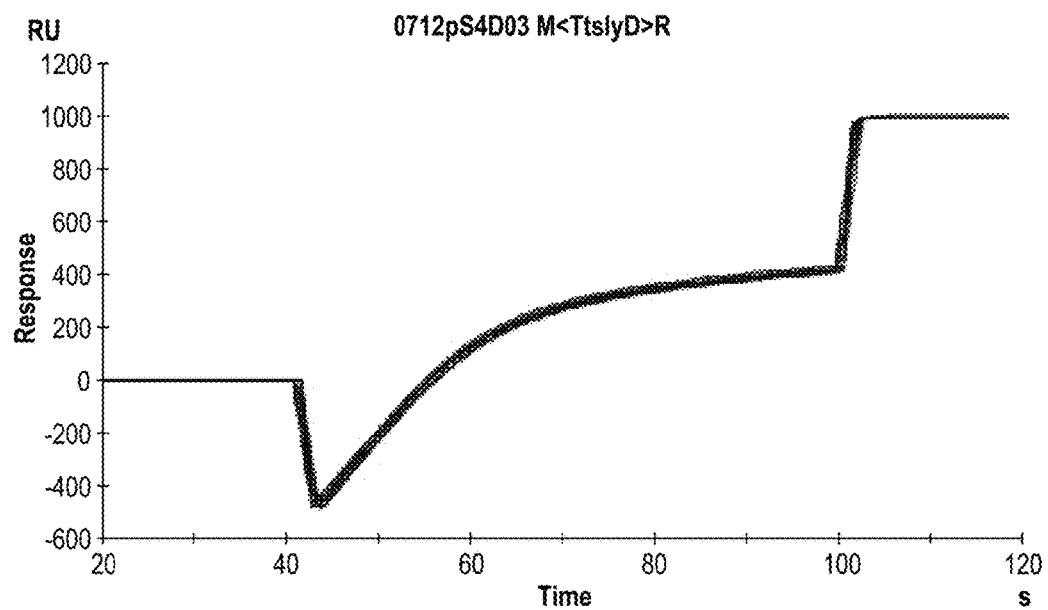

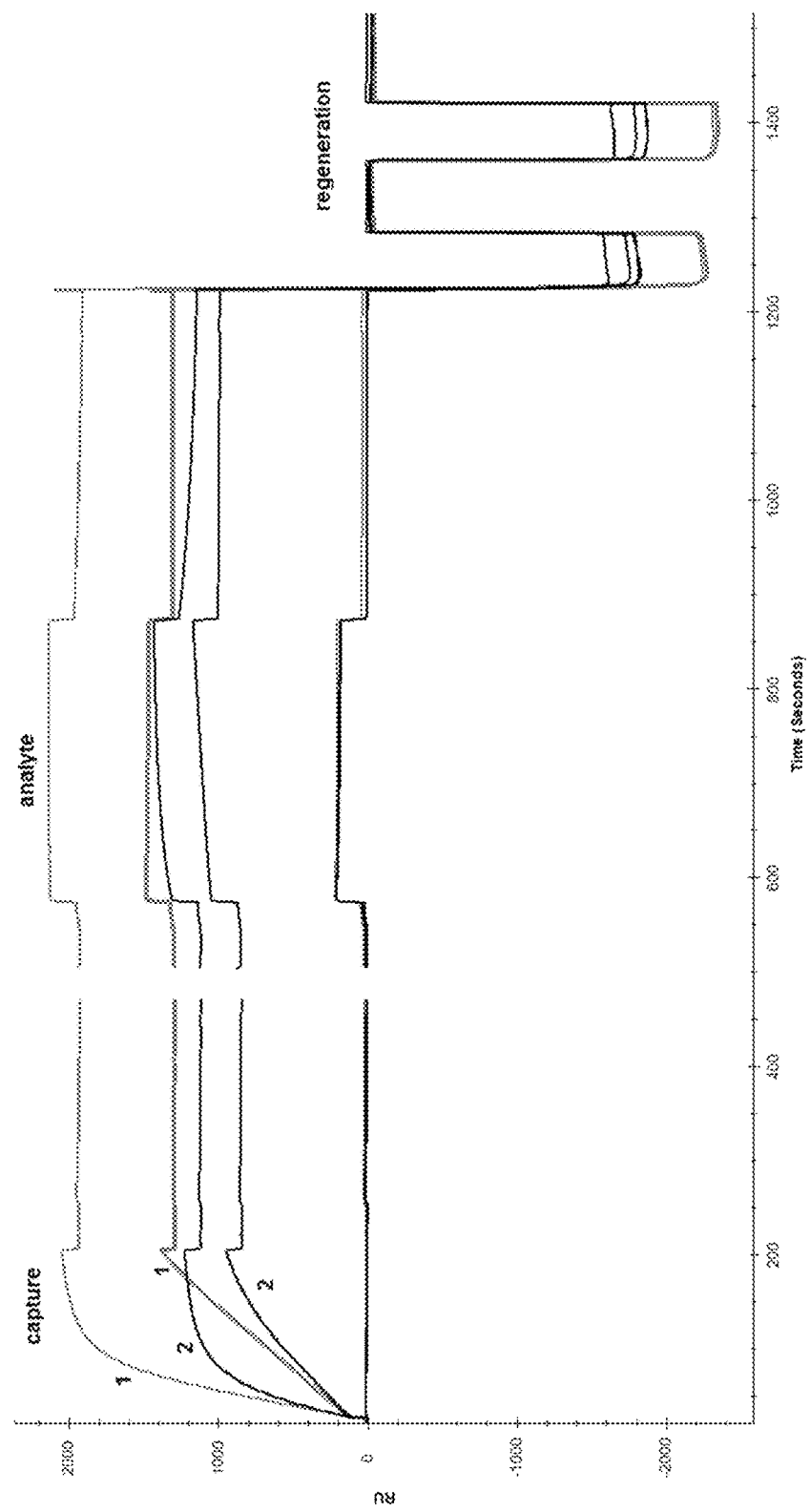

SEQUENCE LISTING

<160> NUMBER OF SEQ ID NOS: 24

<210> SEQ ID NO 1

```
<211> LENGTH: 5
<212> TYPE: PRT
<213> ORGANISM: Oryctolagus cuniculus

<400> SEQUENCE: 1

Gly Asn Ala Leu Ala
1               5

<210> SEQ ID NO 2
<211> LENGTH: 7
<212> TYPE: PRT
<213> ORGANISM: Oryctolagus cuniculus

<400> SEQUENCE: 2

Arg Ala Ser Thr Leu Ala Ser
1               5

<210> SEQ ID NO 3
<211> LENGTH: 12
<212> TYPE: PRT
<213> ORGANISM: Oryctolagus cuniculus

<400> SEQUENCE: 3

Gln Ser Tyr Tyr Asp Ile Tyr Thr Tyr Val Phe Gly
1               5                   10

<210> SEQ ID NO 4
<211> LENGTH: 5
<212> TYPE: PRT
<213> ORGANISM: Oryctolagus cuniculus

<400> SEQUENCE: 4

Ser Asn Ala Ile Ser
1               5

<210> SEQ ID NO 5
<211> LENGTH: 16
<212> TYPE: PRT
<213> ORGANISM: Oryctolagus cuniculus

<400> SEQUENCE: 5

Ile Ile Asn Asn Ile Gly Ser Thr Trp Tyr Ala Ser Trp Ala Lys Gly
1               5                   10                  15

<210> SEQ ID NO 6
<211> LENGTH: 12
<212> TYPE: PRT
<213> ORGANISM: Oryctolagus cuniculus

<400> SEQUENCE: 6

Ile Val Val Asn Tyr Asn Leu Gly Pro Tyr Asn Leu
1               5                   10

<210> SEQ ID NO 7
<211> LENGTH: 5
<212> TYPE: PRT
<213> ORGANISM: Oryctolagus cuniculus

<400> SEQUENCE: 7

Ile Asn Trp Cys Ser
1               5

<210> SEQ ID NO 8
<211> LENGTH: 7
<212> TYPE: PRT
```

```
<213> ORGANISM: Oryctolagus cuniculus

<400> SEQUENCE: 8

Lys Ala Ser Asn Leu Glu Ser
1               5

<210> SEQ ID NO 9
<211> LENGTH: 12
<212> TYPE: PRT
<213> ORGANISM: Oryctolagus cuniculus

<400> SEQUENCE: 9

Gln Gln Gly Tyr Gly Tyr Arg Asp Leu Glu Asn Pro
1               5                   10

<210> SEQ ID NO 10
<211> LENGTH: 5
<212> TYPE: PRT
<213> ORGANISM: Oryctolagus cuniculus

<400> SEQUENCE: 10

Ser Tyr Ala Met Ile
1               5

<210> SEQ ID NO 11
<211> LENGTH: 16
<212> TYPE: PRT
<213> ORGANISM: Oryctolagus cuniculus

<400> SEQUENCE: 11

Val Ile Ser Ser Leu Gly Ile Thr Tyr Tyr Ala Asn Trp Ala Lys Gly
1               5                   10                  15

<210> SEQ ID NO 12
<211> LENGTH: 12
<212> TYPE: PRT
<213> ORGANISM: Oryctolagus cuniculus

<400> SEQUENCE: 12

Gly Phe Phe Ala Gly Gly Ser Asn Tyr Tyr Pro Leu
1               5                   10

<210> SEQ ID NO 13
<211> LENGTH: 105
<212> TYPE: PRT
<213> ORGANISM: Oryctolagus cuniculus

<400> SEQUENCE: 13

Ala Phe Glu Leu Thr Gln Thr Pro Ser Ser Val Glu Ala Ala Val Gly
1               5                   10                  15

Gly Thr Val Thr Ile Lys Cys Gln Ala Thr Glu Asn Ile Gly Asn Ala
                20                  25                  30

Leu Ala Trp Tyr Gln Gln Lys Pro Gly Gln Pro Pro Lys Leu Leu Ile
            35                  40                  45

Tyr Arg Ala Ser Thr Leu Ala Ser Gly Val Pro Ser Arg Phe Lys Gly
        50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Ser Tyr Tyr Asp Ile Tyr Thr
                85                  90                  95

Tyr Val Phe Gly Gly Gly Thr Glu Leu
                100                 105
```

<210> SEQ ID NO 14
<211> LENGTH: 119
<212> TYPE: PRT
<213> ORGANISM: Oryctolagus cuniculus

<400> SEQUENCE: 14

```
Cys Gln Ser Val Glu Glu Ser Gly Gly Arg Leu Val Thr Pro Gly Thr
1               5                   10                  15
Pro Leu Thr Leu Thr Cys Thr Val Ser Gly Phe Ser Leu Ser Ser Asn
            20                  25                  30
Ala Ile Ser Trp Val Arg Gln Ala Pro Gly Lys Gly Leu Glu Trp Ile
        35                  40                  45
Gly Ile Ile Asn Asn Ile Gly Ser Thr Trp Tyr Ala Ser Trp Ala Lys
    50                  55                  60
Gly Arg Phe Thr Ile Ser Lys Ala Ser Ser Thr Val Asp Leu Lys
65                  70                  75                  80
Met Thr Ser Leu Thr Thr Glu Asp Thr Ala Thr Tyr Phe Cys Ala Arg
                85                  90                  95
Ile Val Val Asn Tyr Asn Leu Gly Pro Tyr Asn Leu Trp Gly Pro Gly
            100                 105                 110
Thr Leu Val Thr Val Ser Ser
        115
```

<210> SEQ ID NO 15
<211> LENGTH: 90
<212> TYPE: PRT
<213> ORGANISM: Oryctolagus cuniculus

<400> SEQUENCE: 15

```
Cys Gln Ala Ser Glu Thr Ile Ile Asn Trp Cys Ser Trp Tyr Gln Gln
1               5                   10                  15
Lys Pro Gly Gln Pro Pro Lys Leu Leu Ile Tyr Lys Ala Ser Asn Leu
            20                  25                  30
Glu Ser Gly Val Pro Ser Arg Phe Lys Gly Ser Gly Ser Gly Thr Glu
        35                  40                  45
Phe Thr Leu Thr Ile Ser Asp Leu Glu Cys Ala Asp Ala Ala Thr Tyr
    50                  55                  60
Tyr Cys Gln Gln Gly Tyr Gly Tyr Arg Asp Leu Glu Asn Pro Phe Gly
65                  70                  75                  80
Gly Gly Thr Glu Val Val Val Lys Gly Asp
                85                  90
```

<210> SEQ ID NO 16
<211> LENGTH: 118
<212> TYPE: PRT
<213> ORGANISM: Oryctolagus cuniculus

<400> SEQUENCE: 16

```
Cys Gln Ser Leu Glu Glu Ser Gly Gly Arg Leu Val Lys Pro Gly Gly
1               5                   10                  15
Ser Leu Thr Leu Thr Cys Thr Val Ser Gly Phe Ser Leu Ser Ser Tyr
            20                  25                  30
Ala Met Ile Trp Val Arg Gln Ala Pro Gly Lys Gly Leu Glu Trp Ile
        35                  40                  45
Gly Val Ile Ser Ser Leu Gly Ile Thr Tyr Tyr Ala Asn Trp Ala Lys
    50                  55                  60
```

Gly Arg Phe Thr Ile Ser Lys Ala Ser Thr Thr Val Asp Leu Lys Ile
65                  70                  75                  80

Ala Ser Pro Thr Ile Gly Asp Thr Ala Thr Tyr Phe Cys Ala Arg Gly
                85                  90                  95

Phe Phe Ala Gly Gly Ser Asn Tyr Tyr Pro Leu Trp Gly Pro Gly Thr
            100                 105                 110

Leu Val Thr Val Ser Ser
        115

<210> SEQ ID NO 17
<211> LENGTH: 778
<212> TYPE: DNA
<213> ORGANISM: Oryctolagus cuniculus

<400> SEQUENCE: 17
taacagactg ttcctttcca tgggtctttt ctgcagtcac cgtcgactag ctctgggaga    60
ggagcccagc actagaagtc ggcggtgttt ccattcggtg atcagcactg aacacagagg   120
aagcttgcca ccatggagac tgggctgcgc tggcttctcc tggtcgctgt gctcaaaggt   180
gtccagtgtc agtcggtgga ggagtccggg ggtcgcctgg tcacgcctgg gacacccctg   240
acactcacct gcaccgtctc tggattctcc ctcagtagca tgcaataag ctgggtccgc    300
caggctccag ggaaggggct ggaatggatc ggaatcatta ataatatcgg tagcacatgg   360
tacgcgagct gggcgaaagg ccgattcacc atctccaaag cctcgtcgac acggtggat    420
ctgaaaatga ccagtctgac aaccgaggac acggccacct atttctgtgc aggatagtt    480
gttaattata atcttggccc ctataacttg tggggcccag gcaccctggt caccgtctcc   540
tcagggcaac ctaaggctcc atcagtcttc ccactggccc cctgctgcgg ggacacaccc   600
agctccacgg tgaccctggg ctgcctggtc aaaggctacc tcccgagcc agtgaccgtg    660
acctggaact cgggcaccct caccaatggg gttcgaacct ccccgtccgt ccggcagtcc   720
tcaggcctgt acagcctgag cagcgtggtg agcgtgacct caagcagcca gcccgtca    778

<210> SEQ ID NO 18
<211> LENGTH: 779
<212> TYPE: DNA
<213> ORGANISM: Oryctolagus cuniculus

<400> SEQUENCE: 18
taacagactg ttcctttcca tgggtctttt ctgcagtcac cgtcgactag ctctgggaga    60
ggagcccagc actagaagtc ggcggtgttt ccattcggtg atcagcactg aacacagagg   120
aagcttgcca ccatggacac gagggccccc actcagctgc tggggctcct gctgctctgg   180
ctcccaggtg ccagatgtgc attcgaattg acccagactc catcctccgt ggaggcagct   240
gtgggaggca cagtcaccat caagtgccag gccactgaga cattggcaa tgcattagcc    300
tggtatcagc agaaaccagg gcagcctccc aagctcctga tctataggc atccactctg    360
gcatctgggg tcccatcgcg gttcaaaggc agtggatctg ggacagactt cactctcacc   420
atcagcgacc tggagtgtgc cgatgctgcc acttactact gtcaaagtta ttatgatatt   480
tatacttatg ttttggcgg agggaccgag ctggtggtca aggtgatcc agttgcacct    540
actgtcctca tcttcccacc agctgctgat caggtggcaa ctggaacagt caccatcgtg   600
tgtgtggcga taaatacttt ccccgatgtc accgtcacct gggaggtgga tggcaccacc   660
caaacaactg gcatcgagaa cagtaaaaca ccgcagaatt ctgcagattg tacctacaac   720
ctcagcagca ctctgacact gaccagcaca cagtacaaca gccacaaaga gtacacctg    779

<210> SEQ ID NO 19
<211> LENGTH: 781
<212> TYPE: DNA
<213> ORGANISM: Oryctolagus cuniculus

<400> SEQUENCE: 19

| | | | | | |
|---|---|---|---|---|---|
| taacagactg | ttcctttcca | tgggtctttt | ctgcagtcac | cgtcgactag | ctctgggaga | 60 |
| ggagcccagc | actagaagtc | ggcggtgttt | ccattcggtg | atcagcactg | aacacagagg | 120 |
| aagcttgcca | ccatggacac | gagggccccc | actcagctgc | tggggctcct | gctgctctgg | 180 |
| ctcccaggta | ccagatgtgc | ctatgatatg | acccagactc | cagcctccgt | ggaggcagct | 240 |
| gtgggaggca | cagtcaccat | caattgccaa | gccagtgaga | ccattatcaa | ttggtgttcg | 300 |
| tggtatcagc | agaaaccagg | gcagcctccc | aagctcctga | tctacaaggc | ttccaatctg | 360 |
| gaatctgggg | tcccatcgcg | gttcaaaggc | agtggatctg | gacagagtt | cactctcacc | 420 |
| atcagcgacc | tggagtgtgc | cgatgctgcc | acttactact | gtcaacaggg | ttatggttat | 480 |
| agagatcttg | agaatccttt | cggcggaggg | accgaggtgg | tggtcaaggg | tgatccagtt | 540 |
| gcacctactg | tcctcatctt | cccaccagct | gctgatcagg | tggcaactgg | aacagtcacc | 600 |
| atcgtgtgtg | tggcgaataa | atactttccc | gatgtcaccg | tcacctggga | ggtggatggc | 660 |
| accacccaaa | caactggcat | cgagaacagt | aaaacaccgc | agaattctgc | agattgtacc | 720 |
| tacaacctca | gcagcactct | gacactgacc | agcacacagt | acaacagcca | caaagagtac | 780 |
| a | | | | | | 781 |

<210> SEQ ID NO 20
<211> LENGTH: 778
<212> TYPE: DNA
<213> ORGANISM: Oryctolagus cuniculus

<400> SEQUENCE: 20

| | | | | | |
|---|---|---|---|---|---|
| taacagactg | ttcctttcca | tgggtctttt | ctgcagtcac | cgtcgactag | ctctgggaga | 60 |
| ggagcccagc | actagaagtc | ggcggtgttt | ccattcggtg | atcagcactg | aacacagagg | 120 |
| aagcttgcca | ccatggagac | tgggctgcgc | tggcttctcc | tggtcgctgt | gctcaaaggt | 180 |
| gtccagtgtc | agtcgctgga | ggagtccggg | ggtcgcctgg | tcaagcctgg | aggatccctg | 240 |
| acactcacct | gcacagtctc | tggattctcc | ctcagtagct | atgcaatgat | ctgggtccgc | 300 |
| caggctccag | ggaagggact | ggaatggatc | ggagtcatta | gtagtcttgg | tattacatac | 360 |
| tacgcgaact | gggcgaaagg | ccgattcacc | atctccaagg | cctcgaccac | ggtggatctg | 420 |
| aagatcgcca | gtccgacaat | cggggacacg | gccacctatt | tctgtgccag | aggatttttc | 480 |
| gcaggtggta | gtaattacta | tcccttgtgg | ggccaggca | ccctggtcac | cgtccagtca | 540 |
| ggcaaccta | aggctccatc | agtcttccca | ctggcccct | gctgcgggga | cacacccagc | 600 |
| tccacggtga | ccctgggctg | cctggtcaaa | ggctacctcc | cggagccagt | gaccgtgacc | 660 |
| tggaactcgg | gcaccctcac | caatggggtt | cgaaccttcc | cgtccgtccg | gcagtcctca | 720 |
| ggcctgtaca | gcctgagcag | cgtggtgagc | gtgacctcaa | gcagccagcc | cgtcacct | 778 |

<210> SEQ ID NO 21
<211> LENGTH: 149
<212> TYPE: PRT
<213> ORGANISM: Thermus thermophilus

<400> SEQUENCE: 21

Met Lys Val Gly Gln Asp Lys Val Val Thr Ile Arg Tyr Thr Leu Gln
1               5                   10                  15

Val Glu Gly Glu Val Leu Asp Gln Gly Glu Leu Ser Tyr Leu His Gly
            20                  25                  30

His Arg Asn Leu Ile Pro Gly Leu Glu Glu Ala Leu Glu Gly Arg Glu
        35                  40                  45

Glu Gly Glu Ala Phe Gln Ala His Val Pro Ala Glu Lys Ala Tyr Gly
    50                  55                  60

Pro His Asp Pro Glu Gly Val Gln Val Val Pro Leu Ser Ala Phe Pro
65                  70                  75                  80

Glu Asp Ala Glu Val Val Pro Gly Ala Gln Phe Tyr Ala Gln Asp Met
                85                  90                  95

Glu Gly Asn Pro Met Pro Leu Thr Val Val Ala Val Glu Gly Glu Glu
            100                 105                 110

Val Thr Val Asp Phe Asn His Pro Leu Ala Gly Lys Asp Leu Asp Phe
        115                 120                 125

Gln Val Glu Val Val Lys Val Arg Glu Ala Thr Pro Glu Glu Leu Leu
    130                 135                 140

His Gly His Ala His
145

<210> SEQ ID NO 22
<211> LENGTH: 156
<212> TYPE: PRT
<213> ORGANISM: Thermococcus gammatolerans

<400> SEQUENCE: 22

Met Lys Val Glu Arg Gly Asp Phe Val Leu Phe Asn Tyr Val Gly Arg
1               5                   10                  15

Tyr Glu Asn Gly Glu Val Phe Asp Thr Ser Tyr Glu Ser Val Ala Arg
            20                  25                  30

Glu Gln Gly Ile Phe Val Glu Glu Arg Glu Tyr Ser Pro Ile Gly Val
        35                  40                  45

Thr Val Gly Ala Gly Glu Ile Ile Pro Gly Ile Glu Glu Ala Leu Leu
    50                  55                  60

Gly Met Glu Leu Gly Glu Lys Lys Glu Val Val Pro Pro Glu Lys
65                  70                  75                  80

Gly Tyr Gly Met Pro Arg Glu Asp Leu Ile Val Pro Pro Ile Glu
                85                  90                  95

Gln Phe Thr Ser Ala Gly Leu Glu Pro Val Glu Gly Met Tyr Val Met
            100                 105                 110

Thr Asp Ala Gly Ile Ala Lys Ile Leu Lys Val Glu Glu Lys Thr Val
        115                 120                 125

Arg Leu Asp Phe Asn His Pro Leu Ala Gly Lys Thr Ala Ile Phe Glu
    130                 135                 140

Ile Glu Val Val Glu Ile Lys Lys Ala Gly Glu Ala
145                 150                 155

<210> SEQ ID NO 23
<211> LENGTH: 65
<212> TYPE: PRT
<213> ORGANISM: Thermus thermophilus

<400> SEQUENCE: 23

Met Arg Ser Lys Val Gly Gln Asp Lys Val Val Thr Ile Arg Tyr Thr
1               5                   10                  15

```
Leu Gln Val Glu Gly Glu Val Leu Asp Gln Gly Glu Leu Ser Tyr Leu
            20                  25                  30

His Gly His Arg Asn Leu Ile Pro Gly Leu Glu Glu Ala Leu Glu Gly
        35                  40                  45

Arg Glu Glu Gly Glu Ala Phe Gln Ala His Val Pro Ala Glu Lys Ala
    50                  55                  60

Tyr
65

<210> SEQ ID NO 24
<211> LENGTH: 27
<212> TYPE: PRT
<213> ORGANISM: Thermus thermophilus

<400> SEQUENCE: 24

Gly Lys Asp Leu Asp Phe Gln Val Glu Val Val Lys Val Arg Glu Ala
1               5                   10                  15

Thr Pro Glu Glu Leu Leu His Gly His Ala His
            20                  25
```

*THERMUS THERMOPHILUS* SLYD FKBP DOMAIN SPECIFIC ANTIBODIES

FIELD OF THE INVENTION

The present description relates to anti-*Thermus thermophilus* SlyD FKBP domain antibodies and methods of using the same.

BACKGROUND OF THE INVENTION

In life sciences and in related applied fields there is a need for non-antibody polypeptide molecules capable of performing specific protein-protein interactions. A main focus relies on identifying polypeptide domains that bind to a predetermined target. However, a major obstacle of linear polypeptides comprising about 5 to about 50 amino acids is their intrinsic flexibility. In solution such polypeptides are usually transitioning a large number of structural states that are almost equivalent from an energetic perspective. Nevertheless, such structural states are generally highly dependent on the environment of the polypeptides. As the structural state is an important factor for presenting a certain epitope, e.g. if such polypeptides are used for immunization of an animal for antibody production, it is an essential requirement that the structural state of the polypeptide is not affected by environmental changes, such that an unambiguous presentation of a certain structural state representing a defined epitope can be ensured.

To meet those demands, a protein scaffold can be used where the polypeptide of interest is grafted into a rigid structure. The scaffold forces the polypeptide insertion into an entropy-restricted, structural state, limiting its torsional degrees of freedom. These constructs can be used for applications, such as for the immunization of an experimental animal for producing antibodies against the polypeptide insertion. Furthermore, such a scaffold can be used for the purpose to map antibody epitopes. In another application, such a scaffold can be used as a chimeric calibrator polypeptide for diverse immunological assays. In another application such a scaffold can display constrained peptides with predefined target binding specificity, which allows the scaffold to be used in diverse affinity purification approaches, like affinity chromatography or pull-down assays. In another application, antibody CDR loops can be grafted into such a scaffold. In another application, subdomains of other proteins can be grafted into such a scaffold in order to circularly permutate the chimeric target polypeptide. Domains such as variable loops of antigen binding regions of antibodies have been extensively engineered to produce amino acid sequence segments having improved binding (e.g. affinity and/or specificity) to known targets (e.g. disclosed in Knappik, A. & Plückthun A. J. Mol. Biol. 296 (2000) 57-86; EP 1025218). Engineering of non-antibody frameworks has been reviewed e.g. by Hosse, R. J. et al. Protein Sci., 15 (2006) 14-27. Non-antibody or alternative protein scaffolds have considerable advantages over traditional antibodies due to their small size, high stability, and ability to be expressed in prokaryotic hosts. Novel methods of purification are readily applied; they are easily conjugated to drugs/toxins, penetrate efficiently into tissues and are readily formatted into mono- or multi-specific binders (Skerra, A, et al. J. Mol. Recognit. 13 (2000) 409-410; Binz, H. K. et al. Nature Biotechnol. 23 (2005) 1257-1268).

As known in the art, human FKBP12 can be used as a protein scaffold to improve its enzymatic activity. Knappe, T. A., et al. (J. Mol. Biol. 368 (2007) 1458-1468) reported that the Flap-region of human FKBP12 can be replaced by the IF domain of the structurally related *E. coli* chaperone SlyD. This chimeric FKBP12-IF polypeptide *Thermus thermophiles* SlyD-FKBP has a 200 times increased peptidyl-prolyl-cis/trans isomerase activity (PPI activity) compared to the isolated polypeptide. The *E. coli* SlyD and human FKBP12 (wild type and mutants C23A and C23S) can be recombinantly produced in *E. coli* in high yield in soluble form (Standaert, R. F., et al., Nature 346 (1990) 671-674).

SlyD derived from thermophilic organisms and *E. coli* SlyD can be used as chaperones in the recombinant expression of chimeric polypeptides in *E. coli* (Ideno, A., et al., Appl. Microbiol. Biotechnol. 64 (2004) 99-105). The *E. coli* SlyD and FKBP12 polypeptides are reversibly folding polypeptides (Scholz, C., et al., J. Biol. Chem. 271 (1996) 12703-12707).

The amino acid sequence of the human FKBP12 polypeptide comprises a single tryptophan residue at position 60. Thus, human FKBP12 mutants can be analyzed for structural integrity simply by analyzing the tryptophan fluorescence (DeCenzo, M. T., et al., Protein Eng. 9 (1996) 173-180). A test for remaining catalytic activity of the human FKBP12 mutant can be performed by determining the remaining rotamase activity (Brecht, S., et al., Neuroscience 120 (2003) 1037-1048; Schories, B., et al., J. Pept. Sci. 13 (2007) 475-480; Timerman, A. P., et al., J. Biol. Chem. 270 (1995) 2451-2459). It is also possible to determine the structural integrity of human FKBP12 mutants by determining the FK506- or Rapamycin binding (DeCenzo, M. T., et al., Protein Eng. 9 (1996) 173-180). McNamara, A., et al. (J. Org. Chem. 66 (2001) 4585-4594) report peptides constrained by an aliphatic linkage between two C (alpha) sites: design, synthesis, and unexpected conformational properties of an i,(i+4)-linked peptide.

Suzuki, et al. (Suzuki, R., et al., J. Mol. Biol. 328 (2003) 1149-1160) report the three-dimensional solution structure of an archaic SlyD with a dual function of peptidyl-prolyl-cis-trans isomerase and chaperone-like activities. Expression vector, host, fused polypeptide, process for producing fused polypeptide and process for producing protein are reported in EP 1 516 928. Knappe, T. A., et al., reports that the insertion of a chaperone domain converts human FKBP12 into a powerful catalyst of protein folding (J. Mol. Biol. 368 (2007) 1458-1468). A chimeric polypeptide with superior chaperone and folding activities is reported in WO 2007/077008. In WO 03/000878 the use of SlyD chaperones as expression tool is reported. In EP 1 621 555 an immunogen, composition for immunological use, and method of producing antibody using the same are reported. Rebuzzini, G. (PhD work at the University of Milano-Bicocca (Italy) (2009)) reports a study of the hepatitis C virus NS3 helicase domain for application in a chemiluminescent immunoassay.

In WO 2007/077008 chimeric fusion proteins with superior chaperone and folding activities are reported. The conversion of human FKBP12 into a powerful catalyst of protein folding by insertion of a chaperone domain is reported by Knappe et al. (Knappe, T. A., et al., J. Mol. Biol. 368 (2007) 1458-1468).

WO 2012/150320 discloses a fusion polypeptide comprising one or more fragments of one or more peptidyl-prolyl cis/trans isomerase or FKBP domain family members and its use in methods for antibody screening/selection, for epitope mapping as well as its use as immunogen for the production of antibodies specifically binding an immunogenic peptide or secondary structure presented by the fusion polypeptide.

Among other SlyD chaperones from different species, especially suited is the *Thermus thermophilus* SlyD FKBP domain (herein also referred to as TtSlyD-FKBP) due to its superior biophysical properties regarding thermodynamic stability and solubility (Low et al. (2010) J Mol Biol 398(3): 375-390). The *Thermus thermophilus* SlyD FKBP domain can be used as scaffold for the presentation of constrained peptides WO 2012/150320 which is useful for various applications, such as display methods including phage display, ribosome display, mRNA display and cell surface display. Such methods can be applied to select and optimize target-binding polypeptides from libraries with a large number of candidate amino acid sequences. Another application of the *Thermus thermophilus* SlyD FKBP domain with a certain constrained peptide bound thereto is its use as immunogen for the production of antibodies in animals (WO 2012/150320). Further, the *Thermus thermophilus* SlyD FKBP domain with a certain constrained peptide can be used as a ligand in protein-protein interaction experiments, whereas the constrained peptide represents one specific binding site of the corresponding entire protein binding partner.

These methods and experiments require as a tool an antibody which specifically binds to the *Thermus thermophilus* SlyD FKBP domain (herein referred to as anti-TtSlyD-FKBP antibody). No such antibody is described in the state of the art. The problem to be solved by the present description is therefore the provision of an antibody which binds to the native TtSlyD-FKBP polypeptide.

SUMMARY OF THE INVENTION

The present description relates to anti-TtSlyD-FKBP antibodies and methods of using the same.

In one aspect the description relates to an isolated monoclonal rabbit antibody that binds to TtSlyD-FKBP, wherein the antibody specifically binds to the native conformation of TtSlyD-FKBP.

In one embodiment, the antibody exhibits a ka from $1\times10^3$ 1/Ms to $5\times10^7$ 1/Ms, a kd from $1\times10^{-2}$ 1/s to $1\times10^{-6}$ 1/s, a $t_{1/2d}$ from 1 min to 1500 min and a KD from $1\times10^{-6}$ M to $1\times10^{-13}$ M at a temperature of 25° C. or 37° C.

In a specific embodiment, the antibody comprises (a) HVR-H3 comprising the amino acid sequence of SEQ ID NO:06, (b) HVR-L3 comprising the amino acid sequence of SEQ ID NO:03, and (c) HVR-H2 comprising the amino acid sequence of SEQ ID NO:05, or the antibody comprises (d) HVR-H3 comprising the amino acid sequence of SEQ ID NO:12, (e) HVR-L3 comprising the amino acid sequence of SEQ ID NO:09, and (f) HVR-H2 comprising the amino acid sequence of SEQ ID NO:11.

In another specific embodiment, the antibody comprises (a) HVR-H1 comprising the amino acid sequence of SEQ ID NO:04, (b) HVR-H2 comprising the amino acid sequence of SEQ ID NO:05, and (c) HVR-H3 comprising the amino acid sequence of SEQ ID NO:06, or the antibody comprises (d) HVR-H1 comprising the amino acid sequence of SEQ ID NO:10, (e) HVR-H2 comprising the amino acid sequence of SEQ ID NO:11, and (f) HVR-H3 comprising the amino acid sequence of SEQ ID NO:12.

In yet another specific embodiment, the antibody comprises (a) HVR-L1 comprising the amino acid sequence of SEQ ID NO:01; (b) HVR-L2 comprising the amino acid sequence of SEQ ID NO:02; and (c) HVR-L3 comprising the amino acid sequence of SEQ ID NO:03, or the antibody comprises (d) HVR-L1 comprising the amino acid sequence of SEQ ID NO:07; (e) HVR-L2 comprising the amino acid sequence of SEQ ID NO:08; and (f) HVR-L3 comprising the amino acid sequence of SEQ ID NO:09.

In yet another specific embodiment, the antibody comprises (a) a VH sequence having at least 95% sequence identity to the amino acid sequence of SEQ ID NO:14; (b) a VL sequence having at least 95% sequence identity to the amino acid sequence of SEQ ID NO:13; or (c) a VH sequence as in (a) and a VL sequence as in (b), or the antibody comprises (d) a VH sequence having at least 95% sequence identity to the amino acid sequence of SEQ ID NO:16; (e) a VL sequence having at least 95% sequence identity to the amino acid sequence of SEQ ID NO:15; or (f) a VH sequence as in (d) and a VL sequence as in (e).

In another embodiment, the antibody comprises a VH sequence of SEQ ID NO:14, or wherein the antibody comprises a VH sequence of SEQ ID NO:16. In yet another embodiment, the antibody comprises a VL sequence of SEQ ID NO:13, or wherein the antibody comprises a VL sequence of SEQ ID NO:15.

In another aspect, the description relates to an antibody comprising a VH sequence of SEQ ID NO:14 and a VL sequence of SEQ ID NO:13, or a VH sequence of SEQ ID NO:16 and a VL sequence of SEQ ID NO:15.

In another aspect, the description relates to an antibody that binds to the same epitope as the antibody described herein.

In another aspect, the description relates to isolated nucleic acid encoding the antibody described herein. In one embodiment, the isolated nucleic acid comprises the nucleic acid sequences of SEQ ID NO:17 and SEQ ID NO:18, or the isolated nucleic acid comprises the nucleic acid sequences of SEQ ID NO:19 and SEQ ID NO:20.

In another aspect, the description relates to a host cell comprising the nucleic acids as described in the previous paragraph.

In yet another aspect, the description relates to a method of producing an antibody comprising culturing the host cell of the previous paragraph so that the antibody as described in the present description is produced.

In yet another aspect, the description relates to the use of the antibody as described in the present description in a method, wherein the antibody is used to bind to TtSlyD-FKBP carrying a specific constrained polypeptide.

DESCRIPTION OF THE FIGURES

FIG. 1: The table shows the results of the kinetic analyses of the antibodies 0612pS3A8 and 0712pS4D5. Ab: antibody, nomenclature of the antibody Ab (RU) amount of antibody in relative response units RU, which are captured on the biosensor surface by a polyclonal anti-rabbit capture system. Analyte: analyte injected in solution into the system. MR: Molar Ratio. ka (1/Ms): association rate constant. kd (1/s): dissociation rate constant. KD (nM): Equilibrium dissociation constant. Chi2: error of the measurement. T° C.: temperature of the measurement.

FIG. 2A shows the interaction of the antibody 0612pS3A8 with different TtSlyD-FKBP-A concentrations. FIG. 2B shows the interaction of the antibody 0612pS3A8 with different TtSlyD-FKBP-B concentrations. A Langmuir fitting model is overlaid (grey), Analyte concentrations are labeled at the end of the dissociation curves. The results of the Langmuir evaluation are listed. ka (1/Ms): association rate constant. kd (1/s): dissociation rate constant. KD (nM): Equilibrium dissociation constant. MR: Molar Ratio.

FIG. 3A shows the interaction of the antibody 0712pS4D5 with different TtSlyD-FKBP-A concentrations. FIG. 3B shows the interaction of the antibody 0712pS4D3 with different TtSlyD-FKBP-B concentrations. A Langmuir fitting model is overlaid (grey), Analyte concentrations are labeled at the end of the dissociation curves. The results of the Langmuir evaluation are listed. ka (1/Ms): association rate constant. kd (1/s): dissociation rate constant. KD (nM): Equilibrium dissociation constant. MR: Molar Ratio.

FIG. 4: The figure depicts Biacore binding assays. A: A CM5 sensor was coated with a polyclonal anti-rabbit antibody (black Y-shaped symbol, 1). The respective rabbit monoclonal antibodies 0612pS3A8 or 0712pS4D5 are represented by a greyish Y shaped symbol (2). The TtSlyD-FKBP is represented by the black filled structure (3). The arrows indicate an interaction with recombinant human Taq DNA polymerase (4). B: A CM5 sensor was directly coated with 0612pS3A8 or 0712pS4D5 (1). The TtSlyD-FKBP is represented by the black filled structure (2). An interaction with an analyte in solution (3) can be measured.

FIG. 6: Concentration dependent sensorgram overlay plots of three different TtSlyD-FKBP derivatives with binding activity for Taq DNA polymerase as analyte in solution. A Langmuir fitting model overlays the data. The data was measured with the assay setup depicted in FIG. 4A with antibody 0712pS4D5 as capturing mAb.

FIG. 7: Shown is a table with kinetic data of 0712pS4D5 (RU): antibody captured on the sensor surface by the polyclonal goat anti-rabbit antibody. Scaffold (18 kDa): TtSlyD-FKBP derivatives. MR: Molar Ratio, 0712pS4D5 binds two TtSlyD-FKBP proteins. ka (1/Ms): association rate constant. kd (1/s): dissociation rate constant. KD (nM): Equilibrium dissociation constant. Chi2: error of the measurement. T(° C.) Measurement at 25° C.

FIG. 8: Regeneration Scouting of 0612pS3A8 and 0712pS4D5. Biacore overlay plot of repeated interactions and biosensor surface regenerations of covalently immobilized 0612pS3A8 (top) and 0712pS4D3 with 150 nM TtSlyD-FKBP derivative. Both sensorgrams show the stable binding performance and regeneratability of the 0612pS3A8 and 0712pS4D3 with 10 mM glycine buffer pH 1.7.

FIG. 9: Biacore 4000 kinetic screening overlay sensorgram plot representing the results of a binding assay as depicted in FIG. 4B, where the capture antibodies are directly immobilized on the sensor surface. Capture: Different TtSlyD-FKBP derivatives are injected with stable baseline formation. Analyte: Different analytes are injected. Regeneration: acidic regeneration fully regenerates the capture surface.

DETAILED DESCRIPTION OF THE INVENTION

Figure 2:
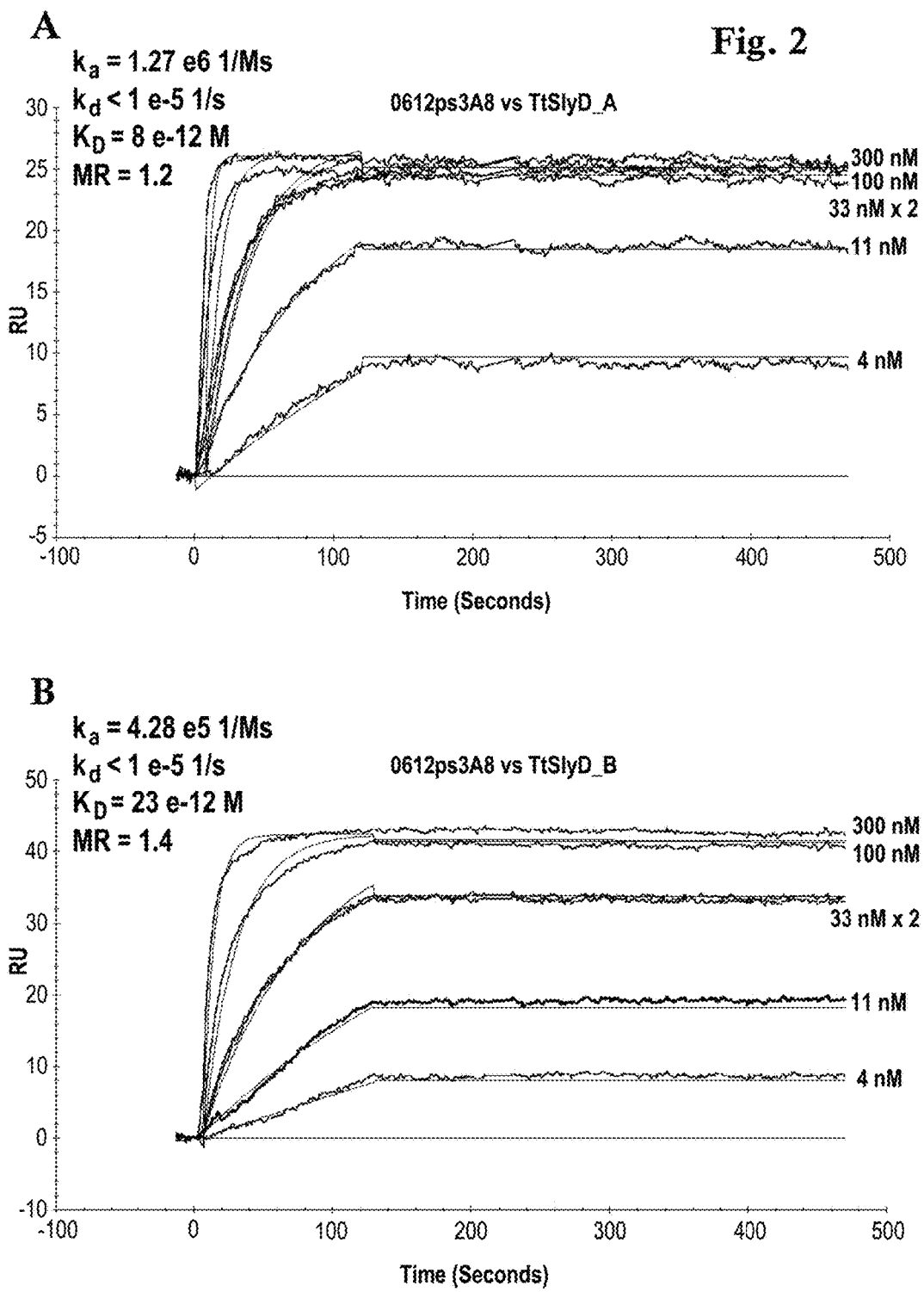
FIG. 2: The Figure depicts a Biacore concentration dependent overlay plot of six increasing analyte concentrations (0 nM, 4 nM, 11 nM, 2×33 nM, 100 nM, 300 nM) of the antibody 0612pS3A8 with two TtSlyD-FKBP derivatives.

The term "about" as used herein in conjunction with a numerical value modifies that value by extending the boundaries above and below the values. In general, the term "about" modifies a numerical value above and below the stated value by a variance of 5% higher or lower. For example a value of "about 100" means a range of "95 to 105".

The terms "affinity", "binding affinity" and "specific binding affinity" refer to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD). Affinity can be measured by common methods known in the art, including those described herein. Specific illustrative and exemplary embodiments for measuring binding affinity are described herein.

The terms "anti-TtSlyD-FKBP antibody" and "an antibody that binds to TtSlyD-FKBP" refers to an antibody that is capable of binding TtSlyD-FKBP (*Thermus thermophilus* SlyD FKBP domain) with sufficient affinity such that the antibody is useful as a diagnostic and/or therapeutic agent in targeting TtSlyD-FKBP. In one embodiment, the extent of binding of an anti-TtSlyD-FKBP antibody to an unrelated, non-TtSlyD-FKBP polypeptide is less than about 10% of the binding of the antibody to TtSlyD-FKBP as measured, e.g., by a radioimmunoassay (MA) or by SPR. In certain embodiments, an antibody that binds to TtSlyD-FKBP has a dissociation constant (KD) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$ M, e.g., from $10^{-9}$M to $10^{-13}$ M).

The term "*Thermus thermophilus* SlyD" or "TtSlyD" refers to a polypeptide that comprises the amino acid sequence SEQ ID No:21.

The term "*Thermococcus gammatolerans* SlyD" refers to a polypeptide that comprises the amino acid sequence SEQ ID No:22.

The term "*Thermus thermophilus* SlyD FKBP" or "TtSlyD-FKBP" refers to a polypeptide that comprise the amino acid sequence SEQ ID NO:23 (part 1) and SEQ ID NO:24 (part 2), wherein both sequences (parts) are linked by $X_1$, (i.e. SEQ ID NO:23-$X_1$-SEQ ID NO:24) and wherein $X_1$ is the amino acid sequence of a linker, or a peptide, or an antigen, or a secondary or tertiary structure to be presented by the *Thermus thermophilus* SlyD fusion polypeptide.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" protein refers to a protein in which a portion of the protein is derived from a particular source or species, while another portion of the protein is derived from a different source or species. In case of the "chimeric TtSlyD-FKBP TtSlyD-FKBP polypeptide" the polypeptide consists of the *Thermus thermophilus* SlyD FKBP domain and a polypeptide graft, which replaces the insert in Flap Domain of the wild type *Thermus thermophilus* SlyD chaperone.

The term "TtSlyD-FKBP" is used herein as known by the person skilled in the art synonymous for the terms "*Thermus thermophilus* SlyD FKBP domain", "T.th.SlyD FKBP domain", "chimeric TtSlyD-FKBP polypeptide", and the like. The term"TtSlyD-FKBP" as used herein refers to the peptidyl-prolyl cis-trans isomerase SlyD as it derives from the extremophile archaebacteria *Thermus thermophilus* (Low et al. (2010) J Mol Biol 398(3): 375-390; Scholz, C., et al. (2006). Biochemistry 45(1): 20-33.) and as it is referred in UNIPROT (Q5SLE7).

TtSlyD-FKBP-A is a 14 kDa derivative of the *Thermus thermophilus* SlyD FKBP domain, wherein the IF domain is replaced by an 8 amino acid insertion.

TtSlyD-FKBP-B is a 21 kDa derivative of the *Thermus thermophilus* SlyD FKBP domain, wherein the IF domain is replaced by a 68 amino acid insertion.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:
(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));
(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));
(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and
(d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see e.g. Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-TtSlyD-FKBP antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present description may be made by a variety of techniques, including but not limited to the hybridoma method, recombinant DNA methods, phage-display methods, and methods utilizing transgenic animals, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See e.g. Portolano, S. et al., J. Immunol. 150 (1993) 880-887; Clackson, T. et al., Nature 352 (1991) 624-628).

In one aspect, an antibody is described that binds to TtSlyD-FKBP, wherein the antibody specifically binds to the native conformation of TtSlyD-FKBP without interfering with the ligand binding site at the insertion site of TtSlyD-FKBP.

Since the antibody binds conformational epitopes aside from the peptide insertion site, they principally can be used in screening approaches, where it is to select and differentiate correctly folded chimeric TtSlyD-FKBP polypeptides from misfolded TtSlyD-FKBP ones. Under the assumption, that misfolded TtSlyD-FKBP polypeptides are instable and prone to, the antibody of the description is useful, e.g., as a tool for detecting intact TtSlyD-FKBP or for detecting stable TtSlyD-FKBP carrying a specific peptide. Thus, in one embodiment, the description refers to the use of the antibody described herein in a method, wherein the antibody is used to bind to intact TtSlyD-FKBP carrying a specific constrained polypeptide. In a specific embodiment, the method is a quality control method for the detection of TtSlyD-FKBP carrying a specific constrained polypeptide.

In one embodiment, TtSlyD-FKBP carrying a specific constrained binding polypeptide can be used in immunological assays for the detection of the binding partner to TtSlyD-FKBP. In a specific embodiment, TtSlyD-FKBP carrying a specific constrained binding polypeptide can be used as ligand immobilized on affinity chromatography media known in the art. After a purification process known in the art the antibody can be used in immunological quality analyses known in the art to determine the absence or presence of TtSlyD-FKBP ligand impurities in the final product. Furthermore, chromatography media known in the art can be surface-functionalized by said antibody in order to generate a multi-purpose chromatography media by capturing TtSlyD-FKBP ligands with different target binding specificities. For that purpose regeneration conditions of the antibodies were optimized. TtSlyD-FKBP derivatives, which present a constrained binding peptide in order to interact, antagonize or agonize protein-protein interactions can also be cloned into fusion polypeptide constructs. The fusion polypeptides can be immunologically detected or purified or pinpointed to diverse surfaces by said antibodies.

In another specific embodiment the antibodies can be used as secondary reagents to detect the presence of TtSlyD-FKBP ligands e.g. on tissue, in IHC experiments, in in vivo imaging studies, in ELISA experiments and in general, in interaction experiments. As it is shown in the examples, the antibodies can be directly coated or indirectly captured on Biosensor surfaces, e.g. SPR, SAW or QCM sensors and TtSlyD-FKBP ligands can be site directed presented on the sensor surface, while the polypeptide insertion in the TtSlyD-FKBP ligand remains accessible for further interacting partners, respectively analytes in solution. It is known in the art, that evolutionary library generation strategies like error prone PCR or the usage of random mutated primers generate a large output of unwanted undefined library members. In another embodiment the antibodies can be used as display targets in TtSlyD-FKBP molecular display approaches in order to enrich in frame TtSlyD-FKBP binding derivatives with intact conformation and stability. This is i.e. of importance to deselect busted TtSlyD-FKBP polypeptides to overcome library quality issues.

A. Exemplary Anti-TtSlyD-FKBP Antibodies

In the following two antibodies capable of binding to TtSlyD-FKBP are described separately, RabMab 0612pS3A8 and RabMab 0712pS4D3.

a) RabMab 0612pS3A8

In one aspect, the description refers to an isolated monoclonal rabbit antibody that binds to TtSlyD-FKBP, wherein the antibody specifically binds to the native conformation of TtSlyD-FKBP. In one embodiment, the isolated monoclonal rabbit antibody binds to TtSlyD-FKBP, wherein the antibody specifically binds to the native conformation of the Thermus thermophilus SlyD FKBP without interfering with the ligand binding site at the insertion site of FKBP domain.

In one embodiment, the isolated antibody that binds to TtSlyD-FKBP has one or more of the following properties (also each combination of each single property is contemplated herein): a) the antibody binds to a conformational epitope in TtSlyD-FKBP in native conformation; and/or b) the antibody exhibits a $k_a$ from $1 \times 10^3$ 1/Ms to $5 \times 10^7$ 1/Ms, and/or c) the antibody exhibits a KD from $1 \times 10^{-2}$ 1/s to $1 \times 10^{-6}$ 1/s, and/or d) the antibody exhibits a $t_{1/2d}$ from 1 min to 1500 min, and/or e) the antibody exhibits a KD from $1 \times 10^{-6}$ M to $1 \times 10^{-13}$ M at a temperature of 25° C. or 37° C.

In a specific embodiment, the isolated antibody that binds to TtSlyD-FKBP has one or more of the following properties (also each combination of each single property is contemplated herein): a) the antibody binds to a conformational epitope in TtSlyD-FKBP in native conformation; and/or b) the antibody exhibits a $k_a$ from $1 \times 10^5$ 1/Ms to $1 \times 10^6$ 1/Ms, and/or c) the antibody exhibits a $k_d$ from $1 \times 10^{-4}$ 1/s to $1 \times 10^{-6}$ 1/s, and/or d) the antibody exhibits a $t_{1/2d}$ from 800 min to 1200 min, and/or e) the antibody exhibits a KD from $1 \times 10^{-10}$ M to $1 \times 10^{-12}$ M at a temperature of 25° C. or 37° C.

In one aspect, an anti-TtSlyD-FKBP antibody is described comprising at least one, two, three, four, five, or six HVRs selected from (a) HVR-H1 comprising the amino acid sequence of SEQ ID NO:04; (b) HVR-H2 comprising the amino acid sequence of SEQ ID NO:05; (c) HVR-H3 comprising the amino acid sequence of SEQ ID NO:06; (d) HVR-L1 comprising the amino acid sequence of SEQ ID NO:01; (e) HVR-L2 comprising the amino acid sequence of SEQ ID NO:02; and (f) HVR-L3 comprising the amino acid sequence of SEQ ID NO:03.

In one aspect, an antibody is described comprising at least one, at least two, or all three VH HVR sequences selected from (a) HVR-H1 comprising the amino acid sequence of SEQ ID NO:04; (b) HVR-H2 comprising the amino acid sequence of SEQ ID NO:05; and (c) HVR-H3 comprising the amino acid sequence of SEQ ID NO:06. In one embodiment, the antibody comprises HVR-H3 comprising the amino acid sequence of SEQ ID NO:06. In another embodiment, the antibody comprises HVR-H3 comprising the amino acid sequence of SEQ ID NO:06 and HVR-L3 comprising the amino acid sequence of SEQ ID NO:03. In a further embodiment, the antibody comprises HVR-H3 comprising the amino acid sequence of SEQ ID NO:06, HVR-L3 comprising the amino acid sequence of SEQ ID NO:03, and HVR-H2 comprising the amino acid sequence of SEQ ID NO:05. In a further embodiment, the antibody comprises (a) HVR-H1 comprising the amino acid sequence of SEQ ID NO:04; (b) HVR-H2 comprising the amino acid sequence of SEQ ID NO:05; and (c) HVR-H3 comprising the amino acid sequence of SEQ ID NO:06.

In another aspect, an antibody is described comprising at least one, at least two, or all three VL HVR sequences selected from (a) HVR-L1 comprising the amino acid sequence of SEQ ID NO:01; (b) HVR-L2 comprising the amino acid sequence of SEQ ID NO:02; and (c) HVR-L3 comprising the amino acid sequence of SEQ ID NO:03. In one embodiment, the antibody comprises (a) HVR-L1 comprising the amino acid sequence of SEQ ID NO:01; (b) HVR-L2 comprising the amino acid sequence of SEQ ID NO:02; and (c) HVR-L3 comprising the amino acid sequence of SEQ ID NO:03.

In another aspect, an antibody according to the description comprises (a) a VH domain comprising at least one, at least two, or all three VH HVR sequences selected from (i) HVR-H1 comprising the amino acid sequence of SEQ ID NO:04, (ii) HVR-H2 comprising the amino acid sequence of SEQ ID NO:05, and (iii) HVR-H3 comprising an amino acid sequence selected from SEQ ID NO:06; and (b) a VL domain comprising at least one, at least two, or all three VL HVR sequences selected from (i) HVR-L1 comprising the amino acid sequence of SEQ ID NO:01, (ii) HVR-L2 comprising the amino acid sequence of SEQ ID NO:02, and (c) HVR-L3 comprising the amino acid sequence of SEQ ID NO:03.

In another aspect, an antibody is described comprising (a) HVR-H1 comprising the amino acid sequence of SEQ ID NO:04; (b) HVR-H2 comprising the amino acid sequence of SEQ ID NO:05; (c) HVR-H3 comprising the amino acid sequence of SEQ ID NO:06; (d) HVR-L1 comprising the amino acid sequence of SEQ ID NO:01; (e) HVR-L2 comprising the amino acid sequence of SEQ ID NO:02; and (f) HVR-L3 comprising an amino acid sequence selected from SEQ ID NO:03.

In another aspect, an anti-TtSlyD-FKBP antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:14. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TtSlyD-FKBP antibody comprising that sequence retains the ability to bind to TtSlyD-FKBP. In certain embodiments, a total of 1 to 10 amino acids have been substituted, inserted and/or deleted in SEQ ID NO:14. In certain embodiments, substitutions, insertions, or deletions occur in regions outside the HVRs (i.e., in the FRs). Optionally, the anti-TtSlyD-FKBP antibody comprises the VH sequence in SEQ ID NO:14, including post-translational modifications of that sequence. In a particular embodiment, the VH comprises one, two or three HVRs selected from: (a) HVR-H1 comprising the amino acid sequence of SEQ ID NO:04, (b) HVR-H2 comprising the amino acid sequence of SEQ ID NO:05, and (c) HVR-H3 comprising the amino acid sequence of SEQ ID NO:06.

In another aspect, an anti-TtSlyD-FKBP antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:13. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TtSlyD-FKBP antibody comprising that sequence retains the ability to bind to TtSlyD-FKBP. In certain embodiments, a total of 1 to 10 amino acids have been substituted, inserted and/or deleted in SEQ ID NO:13. In certain embodiments, the substitutions, insertions, or deletions occur in regions outside the HVRs (i.e., in the FRs). Optionally, the anti-TtSlyD-FKBP antibody comprises the VL sequence in SEQ ID NO:13, including post-translational modifications of that sequence. In a particular embodiment, the VL comprises one, two or three HVRs selected from (a) HVR-L1 comprising the amino acid sequence of SEQ ID NO:01; (b) HVR-L2 comprising the amino acid sequence of SEQ ID NO:02; and (c) HVR-L3 comprising the amino acid sequence of SEQ ID NO:03.

In another aspect, an anti-TtSlyD-FKBP antibody is provided, wherein the antibody comprises a VH as in any of the embodiments provided above, and a VL as in any of the embodiments provided above. In one embodiment, the antibody comprises the VH and VL sequences in SEQ ID NO:14 and SEQ ID NO:13, respectively, including post-translational modifications of those sequences.

In a further aspect, an antibody is described that binds to the same epitope as an anti-TtSlyD-FKBP antibody provided herein. In a specific embodiment, an antibody is provided that binds to the same epitope as an anti-TtSlyD-FKBP antibody comprising a VH sequence of SEQ ID NO:14 and a VL sequence of SEQ ID NO:13. In another specific embodiment, an antibody is provided that binds to the same epitope as an anti-TtSlyD-FKBP antibody comprising at least one, two, three, four, five, or six HVRs selected from (a) HVR-H1 comprising the amino acid sequence of SEQ ID NO:04; (b) HVR-H2 comprising the amino acid sequence of SEQ ID NO:05; (c) HVR-H3 comprising the amino acid sequence of SEQ ID NO:06; (d) HVR-L1 comprising the amino acid sequence of SEQ ID NO:01; (e) HVR-L2 comprising the amino acid sequence of SEQ ID NO:02; and (f) HVR-L3 comprising the amino acid sequence of SEQ ID NO:03.

In a further aspect of the description, an anti-TtSlyD-FKBP antibody according to any of the above embodiments is a monoclonal antibody. In one embodiment, an anti-TtSlyD-FKBP antibody is a monoclonal rabbit antibody. In one embodiment, an anti-TtSlyD-FKBP antibody is an antibody fragment, e.g., a Fv, Fab, Fab', scFv, diabody, or F(ab')$_2$ fragment.

b) RabMab 0712pS4D3

In one aspect, the description refers to an isolated monoclonal rabbit antibody that binds to TtSlyD-FKBP, wherein the antibody specifically binds to the native conformation of TtSlyD-FKBP. In one embodiment, the isolated monoclonal rabbit antibody binds to TtSlyD-FKBP, wherein the antibody specifically binds to the native conformation of TtSlyD-FKBP without interfering with the ligand binding site at the insertion site of TtSlyD-FKBP.

In one embodiment, the isolated antibody that binds to TtSlyD-FKBP has one or more of the following properties (also each combination of each single property is contemplated herein): a) the antibody binds to a conformational epitope in TtSlyD-FKBP in native conformation; and/or b) the antibody exhibits a ka from $1\times10^3$ 1/Ms to $5\times10^7$ 1/Ms, and/or c) the antibody exhibits a kd from $1\times10^{-3}$ 1/s to $1\times10^{-6}$ 1/s, and/or d) the antibody exhibits a $t_{1/2d}$ from 1 min to 1500 min, and/or e) the antibody exhibits a KD from $1\times10^{-6}$ M to $1\times10^{-13}$ M at a temperature of 25° C. or 37° C.

In a specific embodiment, the isolated antibody that binds to TtSlyD-FKBP has one or more of the following properties (also each combination of each single property is contemplated herein): a) the antibody binds to a conformational epitope in TtSlyD-FKBP in native conformation; and/or b) the antibody exhibits a ka from $1\times10^4$ 1/Ms to $1\times10^6$ 1/Ms, and/or c) the antibody exhibits a kd from $1\times10^{-2}$ 1/s to $1\times10^{-6}$ 1/s, and/or d) the antibody exhibits a $t_{1/2d}$ from 10 min to 1200 min, and/or e) the antibody exhibits a KD from $1\times10^{-8}$ M to $1\times10^{-12}$ M at a temperature of 25° C. or 37° C.

In one aspect, an anti-TtSlyD-FKBP antibody is described comprising at least one, two, three, four, five, or six HVRs selected from (a) HVR-H1 comprising the amino acid sequence of SEQ ID NO:10; (b) HVR-H2 comprising the amino acid sequence of SEQ ID NO:11; (c) HVR-H3 comprising the amino acid sequence of SEQ ID NO:12; (d) HVR-L1 comprising the amino acid sequence of SEQ ID NO:07; (e) HVR-L2 comprising the amino acid sequence of SEQ ID NO:08; and (f) HVR-L3 comprising the amino acid sequence of SEQ ID NO:09.

In one aspect, an antibody is described comprising at least one, at least two, or all three VH HVR sequences selected from (a) HVR-H1 comprising the amino acid sequence of SEQ ID NO:10; (b) HVR-H2 comprising the amino acid sequence of SEQ ID NO:11; and (c) HVR-H3 comprising the amino acid sequence of SEQ ID NO:12. In one embodiment, the antibody comprises HVR-H3 comprising the amino acid sequence of SEQ ID NO:12. In another embodiment, the antibody comprises HVR-H3 comprising the amino acid sequence of SEQ ID NO:12 and HVR-L3 comprising the amino acid sequence of SEQ ID NO:09. In a further embodiment, the antibody comprises HVR-H3 comprising the amino acid sequence of SEQ ID NO:12, HVR-L3 comprising the amino acid sequence of SEQ ID NO:09, and HVR-H2 comprising the amino acid sequence of SEQ ID NO:11. In a further embodiment, the antibody comprises (a) HVR-H1 comprising the amino acid sequence of SEQ ID NO:10; (b) HVR-H2 comprising the amino acid sequence of SEQ ID NO:11; and (c) HVR-H3 comprising the amino acid sequence of SEQ ID NO:12.

In another aspect, an antibody is described comprising at least one, at least two, or all three VL HVR sequences selected from (a) HVR-L1 comprising the amino acid sequence of SEQ ID NO:07; (b) HVR-L2 comprising the amino acid sequence of SEQ ID NO:08; and (c) HVR-L3 comprising the amino acid sequence of SEQ ID NO:09. In one embodiment, the antibody comprises (a) HVR-L1 comprising the amino acid sequence of SEQ ID NO:07; (b) HVR-L2 comprising the amino acid sequence of SEQ ID NO:08; and (c) HVR-L3 comprising the amino acid sequence of SEQ ID NO:09.

In another aspect, an antibody according to the description comprises (a) a VH domain comprising at least one, at least two, or all three VH HVR sequences selected from (i) HVR-H1 comprising the amino acid sequence of SEQ ID NO:10, (ii) HVR-H2 comprising the amino acid sequence of SEQ ID NO:11, and (iii) HVR-H3 comprising an amino acid sequence selected from SEQ ID NO:12; and (b) a VL domain comprising at least one, at least two, or all three VL HVR sequences selected from (i) HVR-L1 comprising the amino acid sequence of SEQ ID NO:07, (ii) HVR-L2 comprising the amino acid sequence of SEQ ID NO:08, and (c) HVR-L3 comprising the amino acid sequence of SEQ ID NO:09.

In another aspect, an antibody is described comprising (a) HVR-H1 comprising the amino acid sequence of SEQ ID NO:10; (b) HVR-H2 comprising the amino acid sequence of SEQ ID NO:11; (c) HVR-H3 comprising the amino acid sequence of SEQ ID NO:12; (d) HVR-L1 comprising the amino acid sequence of SEQ ID NO:07; (e) HVR-L2 comprising the amino acid sequence of SEQ ID NO:08; and (f) HVR-L3 comprising an amino acid sequence selected from SEQ ID NO:09.

In another aspect, an anti-TtSlyD-FKBP antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:16. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TtSlyD-FKBP antibody comprising that sequence retains the ability to bind to TtSlyD-FKBP. In certain embodiments, a total of 1 to 10 amino acids have been substituted, inserted and/or deleted in SEQ ID NO:16. In certain embodiments, substitutions, insertions, or deletions occur in regions outside the HVRs (i.e., in the FRs). Optionally, the anti-TtSlyD-FKBP antibody comprises the VH sequence in SEQ ID NO:16, including post-translational modifications of that sequence. In a particular embodiment, the VH comprises one, two or three HVRs selected from: (a) HVR-H1 comprising the amino acid sequence of SEQ ID NO:10, (b) HVR-H2 comprising the amino acid sequence of SEQ ID NO:11, and (c) HVR-H3 comprising the amino acid sequence of SEQ ID NO:12.

In another aspect, an anti-TtSlyD-FKBP antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:15. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TtSlyD-FKBP antibody comprising that sequence retains the ability to bind to TtSlyD-FKBP. In certain embodiments, a total of 1 to 10 amino acids have been substituted, inserted and/or deleted in SEQ ID NO:15. In certain embodiments, the substitutions, insertions, or deletions occur in regions outside the HVRs (i.e., in the FRs). Optionally, the anti-TtSlyD-FKBP antibody comprises the VL sequence in SEQ ID NO:15, including post-translational modifications of that sequence. In a particular embodiment, the VL comprises one, two or three HVRs selected from (a) HVR-L1 comprising the amino acid sequence of SEQ ID NO:07; (b) HVR-L2 comprising the amino acid sequence of SEQ ID NO:08; and (c) HVR-L3 comprising the amino acid sequence of SEQ ID NO:09.

In another aspect, an anti-TtSlyD-FKBP antibody is provided, wherein the antibody comprises a VH as in any of the embodiments provided above, and a VL as in any of the embodiments provided above. In one embodiment, the antibody comprises the VH and VL sequences in SEQ ID NO:16 and SEQ ID NO:15, respectively, including post-translational modifications of those sequences.

In a further aspect, an antibody is described that binds to the same epitope as an anti-TtSlyD-FKBP antibody provided herein. In a specific embodiment, an antibody is provided that binds to the same epitope as an anti-TtSlyD-FKBP antibody comprising a VH sequence of SEQ ID NO:16 and a VL sequence of SEQ ID NO:15. In another specific embodiment, an antibody is provided that binds to the same epitope as an anti-TtSlyD-FKBP antibody comprising at least one, two, three, four, five, or six HVRs selected from (a) HVR-H1 comprising the amino acid sequence of SEQ ID NO:10; (b) HVR-H2 comprising the amino acid sequence of SEQ ID NO:11; (c) HVR-H3 comprising the amino acid sequence of SEQ ID NO:12; (d) HVR-L1 comprising the amino acid sequence of SEQ ID NO:07; (e) HVR-L2 comprising the amino acid sequence of SEQ ID NO:08; and (f) HVR-L3 comprising the amino acid sequence of SEQ ID NO:09.

In a further aspect of the description, an anti-TtSlyD-FKBP antibody according to any of the above embodiments is a monoclonal antibody. In one embodiment, an anti-TtSlyD-FKBP antibody is a monoclonal rabbit antibody. In one embodiment, an anti-TtSlyD-FKBP antibody is an antibody fragment, e.g., a Fv, Fab, Fab', scFv, diabody, or F(ab')$_2$ fragment.

In a further aspect, an anti-TtSlyD-FKBP antibody according to any of the above embodiments may incorporate any of the features, singly or in combination, as described in Sections 1-4 below:

1. Antibody Affinity

In certain embodiments, an antibody provided herein has a dissociation constant KD of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

In one embodiment, KD is measured by a radiolabeled antigen binding assay (RIA) performed with the Fab version of an antibody of interest and its antigen as described by the following assay. Solution binding affinity of FABs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, Y. et al., J. Mol. Biol. 293 (1999) 865-881). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta, L. G. et al., Cancer Res. 57 (1997) 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for 10 min. Concentrations of each Fab that give less than or equal to 20% of maximal binding are chosen for use in competitive binding assays.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody.

Antibody fragments can be made by various techniques, including but not limited to proteolytic digestion of an intact antibody as well as production by recombinant host cells (e.g. *E. coli* or phage), as described herein.

3. Library-Derived Antibodies

Antibodies according to the description may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G. et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned to provide a single source of antibodies to a wide range of non-self and also self antigens without any immunization as described by Griffiths, A. D. et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

4. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Exemplary changes are provided in Table 1 under the heading of "exemplary substitutions", and as further described below in reference to amino acid side chain classes. Conservative substitutions are shown in Table 1 under the heading of "preferred substitutions". Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody. Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or SDRs (a-CDRs), with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Fc Region Variants

In certain embodiments, one or more amino acid modifications may be introduced into the Fc region of an antibody provided herein, thereby generating an Fc region variant. In another embodiment the FC portion can be exchanged by another species, like human, mouse, rabbit, hamster or any other species in order to facilitate a heterogeneous immunoassay. In some embodiments, alterations are made in the Fc region that result in altered (i.e., either improved or diminished) Clq binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

c) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

d) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-TtSlyD-FKBP antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-TtSlyD-FKBP antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-TtSlyD-FKBP antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Anti-TtSlyD-FKBP antibodies provided herein may be identified, screened for, or characterized for their physical/chemical properties and/or biological activities by various assays known in the art.

1. Binding Assays and Other Assays

In one aspect, an antibody according to the description is tested for its antigen binding activity, e.g., by known methods such as ELISA, Western Blot, SPR etc.

In an exemplary competition assay, immobilized TtSlyD-FKBP is incubated in a solution comprising a first labeled antibody that binds to TtSlyD-FKBP and a second unlabeled antibody that is being tested for its ability to compete with the first antibody for binding to TtSlyD-FKBP. The second antibody may be present in a hybridoma supernatant. As a control, immobilized TtSlyD-FKBP is incubated in a solution comprising the first labeled antibody but not the second unlabeled antibody. After incubation under conditions permissive for binding of the first antibody to TtSlyD-FKBP, excess unbound antibody is removed, and the amount of label associated with immobilized TtSlyD-FKBP is measured. If the amount of label associated with immobilized TtSlyD-FKBP is substantially reduced in the test sample relative to the control sample, then that indicates that the second antibody is competing with the first antibody for binding to TtSlyD-FKBP. See Harlow, E. and Lane, D., Antibodies: A Laboratory Manual, Chapter 14, Cold Spring Harbor Laboratory, Cold Spring Harbor, N.Y. (1988).

D. Methods and Compositions for Diagnostics and Detection

In certain embodiments, any of the anti-TtSlyD-FKBP antibodies provided herein is useful for detecting the presence of TtSlyD-FKBP in a biological sample. The term "detecting" as used herein encompasses quantitative or qualitative detection. In certain embodiments, a biological sample comprises a cell or tissue.

In one embodiment, an anti-TtSlyD-FKBP antibody for use in a method of diagnosis or detection is provided. In a further aspect, a method of detecting the presence of TtSlyD-FKBP in a biological sample is provided. In certain embodiments, the method comprises contacting the biological sample with an anti-TtSlyD-FKBP antibody as described herein under conditions permissive for binding of the anti-TtSlyD-FKBP antibody to anti-TtSlyD-FKBP, and detecting whether a complex is formed between the anti-TtSlyD-FKBP antibody and TtSlyD-FKBP. Such method may be an in vitro or in vivo method.

In certain embodiments, labeled anti-TtSlyD-FKBP antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Description of the Amino Acid Sequences
RabMab 0612pS3A8 Sequences:
SEQ ID NO:01 Light chain, HVR-L1, Amino acid sequence
SEQ ID NO:02 Light chain, HVR-L2, Amino acid sequence
SEQ ID NO:03 Light chain, HVR-L3, Amino acid sequence
SEQ ID NO:04 Heavy chain, HVR-H1, Amino acid sequence
SEQ ID NO:05 Heavy chain, HVR-H2, Amino acid sequence
SEQ ID NO:06 Heavy chain, HVR-H3, Amino acid sequence
SEQ ID NO:13 Variable domains light chain (VL), Amino acid sequence
SEQ ID NO:14 Variable domains heavy chain (HL), Amino acid sequence
SEQ ID NO:17 Heavy chain, DNA sequence
SEQ ID NO:18 Light chain, DNA sequence
RabMab 0712pS4D3 Sequences:
SEQ ID NO:07 Light chain, HVR-L1
SEQ ID NO:08 Light chain, HVR-L2
SEQ ID NO:09 Light chain, HVR-L3
SEQ ID NO:10 Heavy chain, HVR-H1
SEQ ID NO:11 Heavy chain, HVR-H2
SEQ ID NO:12 Heavy chain, HVR-H3
SEQ ID NO:15 Variable domains light chain (VL)
SEQ ID NO:16 Variable domains heavy chain (HL)
SEQ ID NO:19 Light chain, DNA sequence
SEQ ID NO:20 Heavy chain, DNA sequence
Other Sequences:
SEQ ID NO:21 *Thermus thermophilus* SlyD, Amino acid sequence
SEQ ID NO:22 *Thermococcus gammatolerans* SlyD, Amino acid sequence
SEQ ID NO:23 *Thermus thermophilus* SlyD FKBP (part 1, see definitions)
SEQ ID NO:24 *Thermus thermophilus* SlyD FKBP (part 2, see definitions)

The following examples 1 to 5 are provided to aid the understanding of the present invention, the true scope of which is set forth in the appended claims.

EXAMPLE 1

Anti-TtSlyD-FKBP Antibody Development with Rabbit B-Cell PCR

For the generation of antibodies against TtSlyD-FKBP, 16-week old ZiKa rabbits were immunized with native TtSlyD-FKBP. All rabbits were subjected to repeated immunizations. In the first months the animals were immunized weekly. From the second month onward the animals were immunized once per month. For each immunization 100 µg TtSlyD-FKBP dissolved in 1 ml 140 mM NaCl was emulsified in 1 ml CFA. The development of titers was evaluated on days 45 and 105 after the first immunization. When titers against the immunogen were detected antibodies were developed by B-cell cloning as described in Ligthwood et al. 2006, Journal of Immunological Methods 316, 133-143. Recombinant rabbit IgG was expressed by transient transfection of HEK293 cells. For the determination of the serum titers against TtSlyD-FKBP a small amount of serum of each rabbit was collected on day 45 and day 105 after start of the immunization campaign. For the ELISA the immunogen was immobilized on the plate surface. TtSlyD-FKBP was immobilized at a concentration of 1 µg/ml. The recombinant protein *Thermococcus gammadurans* SlyD (Uniprot C5A738) was used as a negative control. The sera from each rabbit were diluted in PBS with 1% BSA and the dilutions were added to the plates. The sera were tested at dilutions 1:300, 1:900, 1:2.700, 1:8.100, 1:24.300, 1:72900, 1:218.700 and 1:656.100. Bound antibody was detected with a HRP-labeled F(ab')$_2$ goat anti-rabbit Fcγ (Dianova) and ABTS (Roche) as a substrate.

EXAMPLE 2

Biacore Binding Affinity

Figure 3:
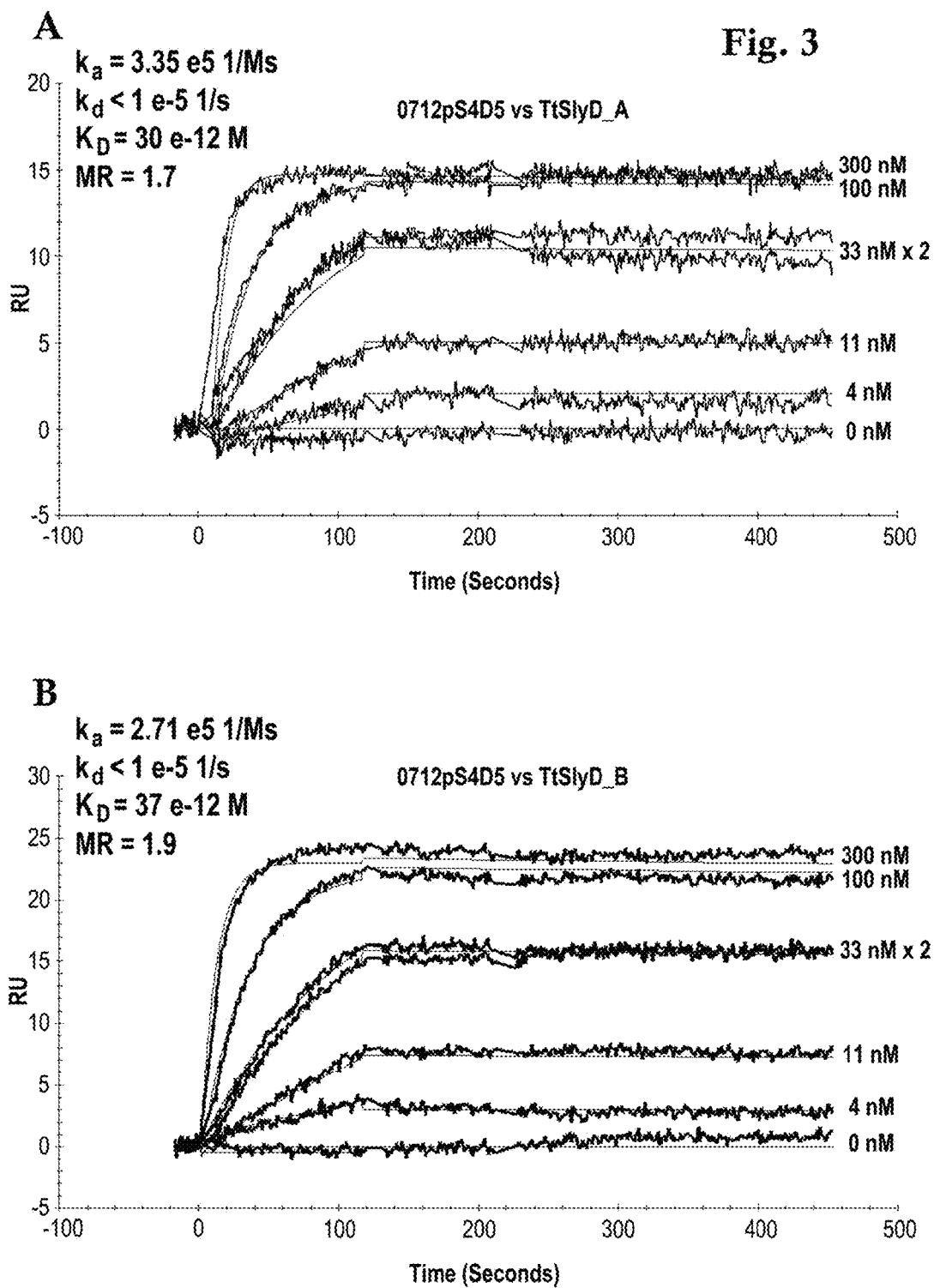
FIG. 3: The Figure depicts Biacore concentration dependent overlay plots of 6 increasing analyte concentrations (0 nM, 4 nM, 11 nM, 2×33 nM, 100 nM, 300 nM) of the antibody 0712pS4D5 with two TtSlyD-FKBP derivatives.

A Biacore B3000 instrument (GE Healthcare) was mounted with a CM5 research grade sensor and was normalized in HBS-ET buffer (10 mM HEPES pH 7.4, 150 mM NaCl, 3 mM EDTA, 0.005% w/v Tween 20) according to the manufacturer's instructions. The system operated at 25° C. 10000 RU GAR-Fcγ (relative units of Fcγ-fragment binding, polyclonal goat anti-Rabbit IgG/Jackson Laboratories) were immobilized according to the manufacturer's instructions using EDC/NHS chemistry on all 4 flow cells. The sensor is finally deactivated using 1 M ethanolamine. 10 nM of the respective antibody 0712pS4D5 or 0612pS3A8 in system buffer were injected for 2 min at 10 µl/min. TtSlyD-FKBP derivatives were injected at 100 µl/min for 2 min association and 5 min dissociation time in a concentration series of 0 nM, 4 nM, 11 nM, two times 33 nM, 100 nM, 300 nM. The GAR-Fcγ capture system was regenerated by 10 mM glycine pH 1.5 at 20 µl/min for 30 sec, followed by two consecutive injections of 10 mM glycine pH 1.7 at 20 µl/min for 30 sec. Affinity was determined using the Biacore evaluation software. The results of the kinetic analyses are depicted in FIG. 1. The analytes in solution were two engineered TtSlyD-FKBP, TtSlyD-FKBP-A and TtSlyD-FKBP-B. The Molar Ratio (MR) indicates a functional binding. 0612pS3A8 binds in a 1:1 ratio and 0712pS4D5 bind two scaffolds in a 1:2 mode. Therefore different binding sterics of the two antibodies can be assumed. The complex stability was too high and was therefore out of the instruments specifications. To calculate an apparent affinity the dissociation rate was set to the instrument limits of 1e-05 1/s. Therefore, the affinity is in the low picomolar range. FIG. 2 depicts Biacore sensorgrams showing the 0612pS3A8 interactions with two different TtSlyD-FKBP derivatives. FIG. 3 depicts Biacore sensorgrams showing the 0712pS4D5 interactions with two different TtSlyD-FKBP derivatives. Concentration-dependent sensorgram overlay plots of 0612pS3A8 are in FIG. 2, and for 0712pS4D5 in FIG. 3.

EXAMPLE 3

Biacore Binding Assay

FIG. 4 shows the instrumental setup of a Biacore SPR binding assay. For such assay, a Biacore B3000 instrument (GE Healthcare) was used to kinetically assess TtSlyD-FKBP derivatives for binding specificity for Taq DNA polymerase A CM5 series sensor was mounted into the system and was normalized in HBS-ET buffer (10 mM HEPES pH 7.4, 150 mM NaCl, 3 mM EDTA, 0.005% w/v Tween 20) according to the manufacturer's instructions. The system operated at 25° C. 10000 RU GAR-Fcγ (relative units of Fcγ-fragment binding, polyclonal goat anti-Rabbit IgG/ Jackson Laboratories) were immobilized according to the manufacturer's instructions using EDC/NHS chemistry on all 4 flow cells. The sensor was finally deactivated using 1 M ethanolamine.

The binding activity of the TtSlyD-FKBP clones 3 F12, 5F8 and 3 C1 versus Taq DNA polymerase was kinetically tested. The monoclonal rabbit anti-TtSlyD-FKBP antibody (0612pS3A8), was captured in all flow cells by a 3 min injection at 30 µl/min. Each TtSlyD-FKBP variant was captured on the flow cells 2, 3 and 4. Flow cell 1 served as a reference. The TtSlyD-FKBP clones were specifically captured on the sensor by a 3 min injection at 10 µl/min. The flow rate was set to 80 µl/min. Recombinant 93 a Taq DNA polymerase (Roche) was injected for 3 min at different concentration steps diluted in the sample buffer at 0 nM, 4 nM, 11 nM, two times 33 nM, 100 nM and 300 nM. 1 µM Streptavidin (Ser. No. 11/897,000, Roche) was injected as a non-interaction specificity control. The dissociation was monitored for 5 min. FIG. 6 shows Biacore sensorgram overlay plots of three TtSlyD-FKBP derivatives interacting with Taq DNA polymerase at different concentrations. FIG. 7 shows the kinetic data determined according to a Langmuir model.

Acidic regeneration of the sensor surface was achieved using a single injection of 10 mM glycine pH 1.5 at 20 µl/min for 30 sec, followed by two consecutive injections of 10 mM glycine pH 1.7 at 20 µl/min for 30 sec. Regeneration was complete.

Figure 5:
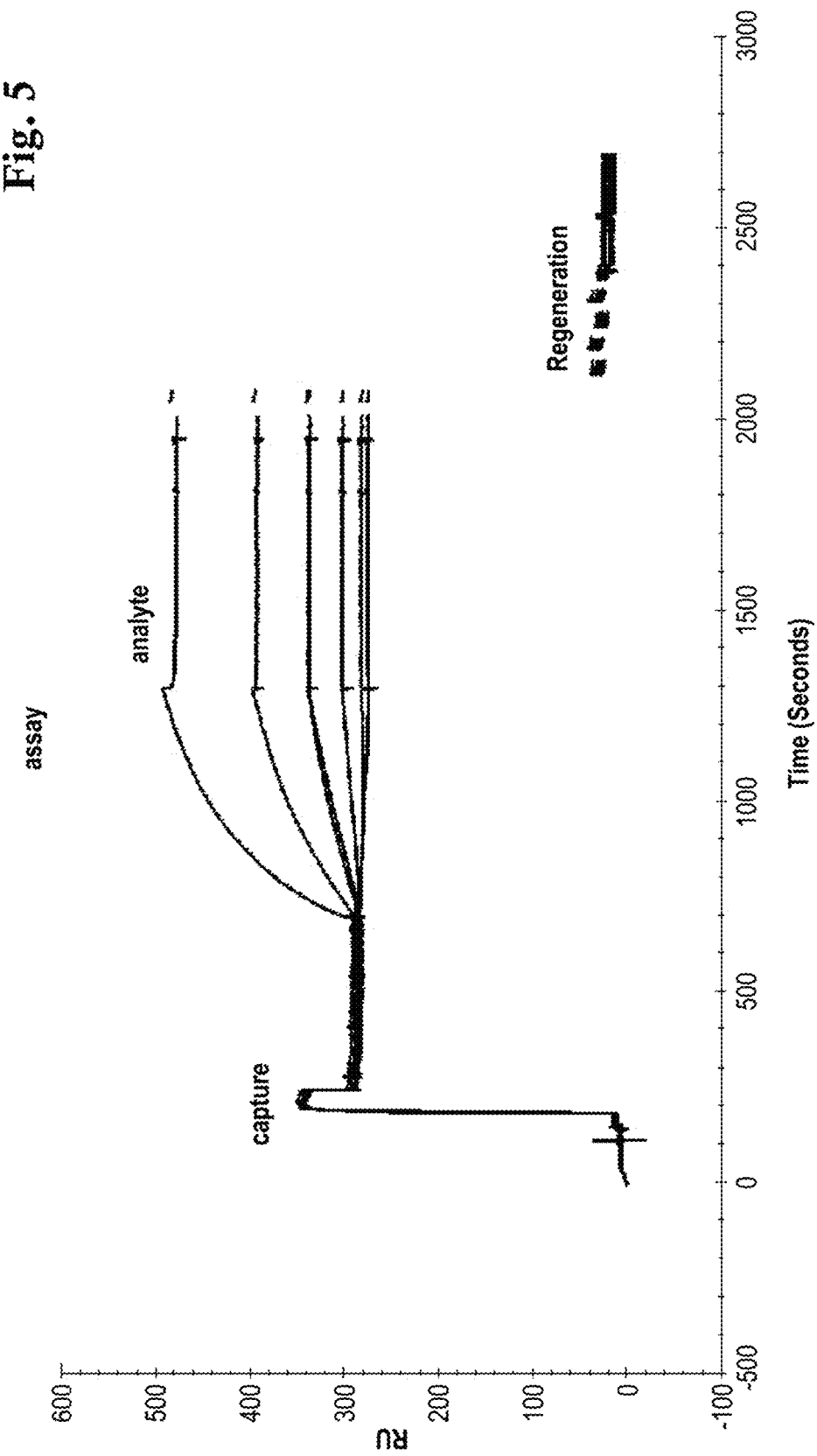
FIG. 5: The overlay sensorgram represents the results of the SPR binding assay as depicted in FIG. 4A. Capture: TtSlyD-FKBP injection and stable presentation. Analyte: Different analyte concentrations are injected. Regeneration: acidic regeneration fully regenerates the goat anti-rabbit polyclonal capture surface.

As can be seen in FIG. 5, the overlay plot sensorgram shows six exemplary consecutive cycles of the SPR binding assay as depicted in FIG. 4. Capture denotes the injection of the TtSlyD-FKBP variant 3C1 and shows the reproducibility of the scaffold capturing step. Analyte denotes the injection of Taq DNA polymerase.

Each cycle injects an increasing Taq DNA polymerase concentration as described. Regeneration denotes the acidic regeneration of the sensor surface. Since Taq DNA polymerase was displayed as chemically biotinylated target protein on streptavidin coated paramagnetic particles, it was necessary to investigate potential streptavidin cross-reactive binding. No streptavidin binding to the variants could be detected at 1 µM streptavidin as analyte in solution.

EXAMPLE 4

Biacore Binding Study with Covalently Immobilized 0712pS4D5 and 0612pS3A8

A Biacore B3000 instrument (GE Healthcare) was mounted with a CM5 sensor and was normalized in HBS-ET buffer (10 mM HEPES pH 7.4, 150 mM NaCl, 3 mM EDTA, 0.005% w/v Tween 20) according to the manufacturer's instructions.

Both antibodies, 0712pS4D5 and 0612pS3A8 were incubated at 30 µg/ml in 10 mM NaAc pH 4.0, respectively pH 4.5, pH 5.0, pH 5.5 and were preconcentrated on the CM-5 sensor, followed by NHS-ECD immobilization according to the manufacturer's instructions.

10 mM NaAc pH 4.5 and 30 µg/ml antibody concentration was found the optimal condition for the immobilization of 10.000 RU of each antibody on the CM-5 sensor.

150 nM of the TtSlyD-FKBP derivative 5CRe1 was injected into the system for 5 min at 100 µl/min. The dissociation was monitored for another 5 min. The system was regenerated with 10 mM glycine buffer pH 1.7 at 20 µl/min for 1 min. Using this condition the immobilized antibodies are keeping their binding activity over 20 cycles of binding and regeneration. Therefore it is assumed, that the respective regeneration condition is optimal to keep up the antibodies binding activity. FIG. 8 shows regeneration scouting of 0712pS4D5 and 0612pS3A8.

EXAMPLE 5

Kinetic Screening with Covalently Surface-Attached Antibodies

A Biacore 4000 instrument is mounted with a Biacore CM 5 sensor series S and was preconditioned like recommended by the manufacturer. The instrument buffer was HBS-ET (10 mM HEPES pH 7.4, 150 mM NaCl, 3 mM EDTA, 0.005% w/v Tween 20). The rabbit monoclonal antibodies, 0712pS4D5 and 0612pS3A8 were covalently immobilized on the sensor surface by using the standard amine coupling procedure as recommended by the manufacturer. The antibodies were each incubated at 30 µg/ml in 10 mM NaAc pH 4.5 and were preconcentrated on the CM-5 sensor for 10 min, followed by NHS-ECD immobilization according to the manufacturer's instructions. In average 8500 RU antibody were immobilized on the sensor spots 1, 2, 4 and 5 on the flow cells 1, 2, 3, and 4. Spot 3 serves as a reference.

Subsequently different TtSlyD-FKBP derivatives were injected at 10 µl/min for 3 min and were stably bound by the surface immobilized antibodies 0712pS4D5 on the flow cells 1 and 2 or 0612pS3A8 on the flow cells 3 and 4. FIG. 9 shows a sensorgram overlay plot of 4 exemplary injections with 0712pS4D5 as capture antibody numbered with (1) and 0612pS3A8 as capturing antibody numbered with (2). Both antibodies bind different TtSlyD-FKBP based scaffold binders with high complex stability and stable baseline formation. This is of upmost importance to enable a kinetic measurement without any baseline drift. The surface presented scaffold binders are subsequently contacted with an analyte in solution. The analyte is injected for 5 min and dissociates for another 5 min at 30 The surface is fully regenerated by two injections of 10 mM glycine buffer pH 1.7 and the sensor is reusable.

To summarize, the rabbit monoclonal antibodies 0712pS4D5 and 0612pS3A8 can be used in a Biacore Kinetic Screening setup with a GAR-Fcγ capture system, which displays the rabbit antibodies via their FC portion. The antibodies bind to TtSlyD-FKBP derivatives with a 1:2 stoichiometry and with high complex stability, respectively picomolar affinity. The rabbit antibodies bind to an epitope of the TtSlyD-FKBP derivatives, which functionally displays the scaffolds, so that they can form a complex (sandwich) with further binding partners, like e.g. Taq DNA polymerase.

Another option is to directly immobilize the antibodies on the biosensor surface using NHS-EDC chemistry, whereby the optimal regeneration condition is a 10 mM glycine buffer pH 1.7. Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An isolated monoclonal rabbit antibody that binds to *Thermus thermophilus* SlyD FKBP (TtSlyD-FKBP), wherein the antibody comprises a VH sequence of SEQ ID NO: 14 and a VL sequence of SEQ ID NO: 13, and wherein the antibody specifically binds to the native conformation of TtSlyD-FKBP.

2. An isolated monoclonal rabbit antibody that binds to TtSlyD-FKBP, wherein the antibody comprises a L1 sequence of SEQ ID NO: 1, L2 sequence of SEQ ID NO: 2, L3 sequence of SEQ ID NO: 3, H1 sequence of SEQ ID NO: 4, H2 sequence of SEQ ID NO: 5, H3 sequence of SEQ ID NO: 6, VL sequence of SEQ ID NO: 13, and VH sequence of SEQ ID NO: 14, and wherein the antibody specifically binds to the native conformation of TtSlyD-FKBP.

3. An isolated monoclonal rabbit antibody that binds to TtSlyD-FKBP, wherein the antibody comprises an H sequence of SEQ ID NO: 17 and an L sequence of SEQ ID NO: 18, and wherein the antibody specifically binds to the native conformation of TtSlyD-FKBP.

* * * * *